(12) United States Patent
Zou et al.

(10) Patent No.: US 12,098,371 B2
(45) Date of Patent: Sep. 24, 2024

(54) LIPID-PEGYLATED COMPOUNDS, PREPARATIONS AND USES THEREOF

(71) Applicant: Hongene Biotech Corporation, Union City, CA (US)

(72) Inventors: Mufa Zou, Ellicott City, MD (US); David Yu, Union City, CA (US); Aldrich N. K. Lau, Palo Alto, CA (US); Ruiming Zou, Foster City, CA (US); Wing C. Poon, Union City, CA (US); Gang Zhao, Union City, CA (US); Gengyu Du, Union City, CA (US); Yun-Chiao Yao, Union City, CA (US); Allen Wong, Union City, CA (US); Xiaojun Li, Union City, CA (US)

(73) Assignee: Hongene Biotech Corporation, Union City, CA (US)

( * ) Notice: Subject to any disclaimer, the term of this patent is extended or adjusted under 35 U.S.C. 154(b) by 0 days.

(21) Appl. No.: 18/451,013

(22) Filed: Aug. 16, 2023

(65) Prior Publication Data

US 2024/0117362 A1 Apr. 11, 2024

Related U.S. Application Data

(60) Provisional application No. 63/371,915, filed on Aug. 19, 2022.

(51) Int. Cl.
*C12N 15/117* (2010.01)
*B01J 19/00* (2006.01)

(52) U.S. Cl.
CPC .......... *C12N 15/117* (2013.01); *B01J 19/0046* (2013.01); *C12N 2310/14* (2013.01); *C12N 2310/17* (2013.01); *C12N 2310/3515* (2013.01)

(58) Field of Classification Search
CPC .......................... C12N 15/117; C12N 2310/14; C12N 15/113; C12N 15/11; C12N 2310/11; B01J 19/0046
See application file for complete search history.

(56) References Cited

U.S. PATENT DOCUMENTS 4,307,079 A 12/1981 Zorayan et al.
2019/0185855 A1* 6/2019 Khvorova ............ A61K 47/548

FOREIGN PATENT DOCUMENTS

WO WO 2008/028206 3/2008
WO WO 2014/169264 10/2014
WO WO 2018/031933 2/2018

OTHER PUBLICATIONS

Glen Research, "The Glen Report" 2012, vol. 24, No. 1, pp. 1-12. (Year: 2012).*
Wolfrum, C.; et al. "Mechanisms and optimization of in vivo delivery of lipophilic siRNAs" 2007, Nature Biotechnology, vol. 5, pp. 1149-1157. (Year: 2007).*
Glen Research, "The Glen Report" 2016, vol. 28, No. 1, pp. 1-12. (Year: 2016).*
Pon, R. T.; Yu, S. "Rapid Automated Derivatization of Solid-Phase Supports For Oligonueleotide Synthesis Using Uronium or Phosphonium Coupling Reagents" 1997, Tetrahedron Letters, vol. 19, pp. 3331-3334. (Year: 1997).*
Carey, 1992, Organic Chemistry, 2d ed., McGraw-Hill, Inc., New York, pp. 328-331.
CAS RN: 52656-49-2; Date Entered STN: Nov. 16, 1984: α-[4-[2-hydroxy-3-[(2-methyl-1-oxo-2-propenyl)oxy]propoxy]-1,4-dioxobutyl]-ω-[2-[(1-oxotridecyl)amino]ethoxy]poly(oxy-1,2-ethanediyl).
McManus, et al., Oct. 2002, Gene silencing in mammals by interfering RNAs, Nat. Rev. Genet., 3:737-747.
McMurry, 2000, Organic Chemistry, 5th ed., Brooks/Cole, Pacific Grove, CA, pp. 398 and 408.
Osborn et al., 2018, Improving siRNA delivery in vivo through lipid conjugation, Nucleic Acid Therapeutics 28(3):128-36.
Scheit, 1980, Nucleotide analogs: Synthesis and biological function. New York: John Wiley & Sons (TOC).
Streitwieser et al., 1981, Introduction to Organic Chemistry, 2d ed., Macmillan Publishing Co., Inc., New York, pp. 169-171.
Uhlman et al., Jun. 1990, Antisense oligonucleotides: a new therapeutic principle, Chemical Reviews, 90(4):543-584.
Winkler, 2015, Therapeutic oligonucleotides with polyethylene glycol modifications, Future Medicinal Chemistry 7(13):1721-1731.
International Search Report and Written Opinion dated Nov. 1, 2023 in international application No. PCT/US2023/072270, filed Aug. 16, 2023.

* cited by examiner

*Primary Examiner* — Eric Olson
*Assistant Examiner* — Benjamin M Brandsen
(74) *Attorney, Agent, or Firm* — Knobbe, Martens, Olson & Bear, LLP

(57) ABSTRACT

Embodiments of the present disclosure relate to lipid-PEGylated solid support and phosphoramidites derivatives, methods for preparing the same, and their uses in the delivery of oligonucleotide drugs to the cellular targets.

27 Claims, 1 Drawing Sheet
Specification includes a Sequence Listing.

```
                          SEQUENCE LISTING

Sequence total quantity: 1
SEQ ID NO: 1              moltype = DNA  length = 10
FEATURE                   Location/Qualifiers
source                    1..10
                          mol_type = other DNA
                          organism = synthetic construct
SEQUENCE: 1
tttttttttt                                                              10
```

LIPID-PEGYLATED COMPOUNDS, PREPARATIONS AND USES THEREOF

FIELD

The present disclosure relates to lipid-PEGylated solid support and phosphoramidites derivatives, methods for preparing the same, and their uses in the delivery of oligonucleotide drugs.

REFERENCE TO SEQUENCE LISTING

The present application is being filed along with a Sequence Listing in electronic format. The Sequence Listing is provided as a file entitled "HGENE021A_Sequence_Listing.xml" created on Aug. 10, 2023, which is 1.90 KB in size. The information in the electronic format of the Sequence Listing is incorporated herein by reference in its entirety.

BACKGROUND

Oligonucleotides can be used in a variety of applications, including as therapeutics for diseases. During synthesis, specific nucleotides can be combined in any desired order. Because oligonucleotides are customizable, they can be used to target molecules that cannot be controlled by normal drugs, such as messenger RNA (mRNA) or noncoding RNA. This allows for targeted treatment of diseases such as cancer and genetic disorders through therapies such as antisense and small interfering RNA (siRNA) therapies.

siRNAs exhibit unique properties, such as high potency, specificity, and no interferon response. siRNAs have been proved to be effective tools for gene silencing, and have found their uses in therapeutic applications since early 2000s (McManus, et al., "Gene silencing in mammals by interfering RNAs" *Nat. Rev. Genet.* 2002, 3, 737). Effective delivery of the oligos to the cellular targets has always been the biggest challenge. siRNAs are large, polyanionic macromolecules with poor pharmacological properties. siRNAs have a half-life of less than five minutes in circulation and are unable to permeate intact cellular membranes. These challenges may be overcome by combining siRNAs with hydrophobic molecules such as hydrophobic polymers or lipids. In vivo studies demonstrated that the conjugation of a lipophilic group, such as long-chain fatty acid or cholesterol, to an oligonucleotide to form a lipid-oligonucleotide conjugates (LON) may enhance its uptake into the cells.

There are two major ways to synthesize LONs: a pre-synthetic approach and a post-synthetic approach. For the pre-synthetic approach, a hydrophobic moiety is already bound to a solid support before the oligonucleotide is constructed. In the post-synthetic approach, the oligonucleotide is constructed and then the hydrophobic moiety is attached. Both approaches have their own challenges. The post-synthetic approach requires certain reactive groups on the oligonucleotide and lipid in order to combine them. The pre-synthetic approach utilizes solid-phase synthesis to attach the hydrophobic moiety to the oligonucleotide, making it easier to purify than the post-synthetic approach. However, the pre-synthetic approach is limited by the solubility and stability requirements and challenges that arise from introducing hydrophobic moieties directly into the solid-phase oligonucleotide synthesis.

PEGylation is a well-established strategy in the field of oligonucleotides to increase circulation lifetimes, prevent enzymatic degradation, and avoid rapid renal elimination. Winkler, *Future Medicinal Chemistry* 7:1721-31, 2015. Among the most important challenges in the development of oligonucleotide therapeutics is their polyanionic and highly hydrophilic character. This leads to very short circulation times in vivo (e.g., on the order of minutes). The lipidation of oligonucleotides significantly increases their hydrophobic character and provides for longer circulation times, in addition to other benefits including enhanced self-assembly and cellular uptake. Li et al., *Nucleic Acid Therapeutics* 28:128-36, 2018. To this end, PEGylation, and the specific length of the PEG linker relative to the lipid chain, can have important effects on the overall solubility of the LON complex. PEG is amphiphilic, and the ability to control the number of —$CH_2OH$— units may allow for a fine-tuning of water solubility. This precise tuning, in turn, may be important for modulating both pharmacokinetic and pharmacodynamic properties.

The PEG linker may also modulate a LON's water solubility through unique structural mechanisms. For example, PEG's high flexibility is believed to lead to the creation of a hydration layer, which not only increases overall solubility but also increases the hydrodynamic volume, potentially shielding it from degradative proteins. Another advantage of PEG is its high bioavailability, which is believed to have standalone effects of prolonged circulation time, reduced degradation and, at least for smaller molecules, reduced renal filtration.

With respect to oligonucleotides, PEGylation can be achieved by using standard chemical conjugation methods, by using disulfide or maleimide linkages, or by copper-free click chemistry. Moreover, PEG's chemically inert backbone allows for chemical modification only at the terminal sites, which is highly convenient for tethering to solid supports or for conjugation of biomolecules. The specific length of the PEG linker appears to be important to modulating therapeutic efficiency of siRNAs. siRNAs with PEG chains with a length of between 5 and 20 kDa attached at the 5' end of the sense strand showed a significant reduction in in vitro gene silencing activity compared with unmodified siRNA, while using shorter PEG chains did not significantly compromise gene-silencing efficiency. Winkler at 1724.

The present application discloses preparation of lipid-PEGylated solid support as well as lipid-PEGylated phosphoramidites for use to synthesize LONs under both pre-synthetic and post-synthetic approaches. In particular, the lipid moiety may contain fatty acid moieties and shorter PEG chains, which may provide improved drug distribution after injection than cholesterol and tocopherol-conjugated siRNA.

SUMMARY

One aspect of the present application relates to a compound of formula (I):

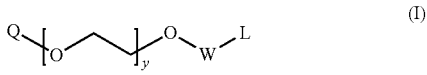

Wherein Q is

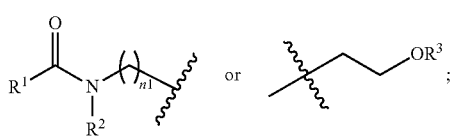

W is $C_{1-10}$ alkylene, 2 to 10 membered heteroalkylene, or

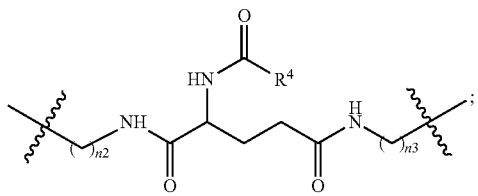

L is

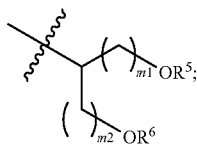

each of $R^1$ and $R^4$ is independently $C_{1-22}$ alkyl or $C_{2-22}$ alkenyl;

$R^2$ is H, $C_{1-6}$ alkyl or

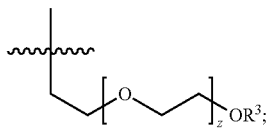

each of $R^3$ and $R^5$ is independently H or a hydroxyl protecting group;

$R^6$ is hydrogen, a phosphoramidite moiety, —C(=O)CH$_2$CH$_2$C(=O)R$^{6A}$, or —P(OR$^{6B}$)NR$^{6C}$R$^{6D}$;

$R^{6A}$ is —OH, —OR$^7$ or —NR$^8$R$^9$;

each of $R^{6B}$, $R^{6C}$ and $R^{6D}$ is independently H, $C_{1-6}$ haloalkyl, or optionally substituted $C_{1-6}$ alkyl;

$R^7$ is optionally substituted $C_{1-6}$ alkyl or a hydroxy protecting group; and each of $R^8$ and $R^9$ is independently H, optionally substituted $C_{1-6}$ alkyl or an amino protecting group;

each of y and z is independently an integer of 1 to 100;

each of n1, n2 and n3 is independently an integer of 1 to 10; and p each of m1 and m2 is independently 0, 1, 2 or 3;

provided that when Q is

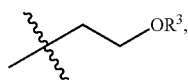

then W is

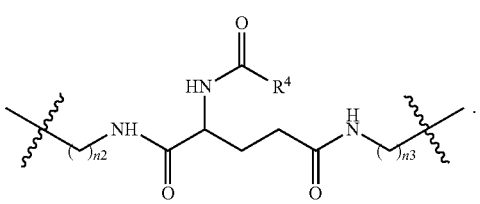

In some embodiments, the compounds of Formula (I) may also have the structure of Formula (Ia), (Ib) or (Ic):

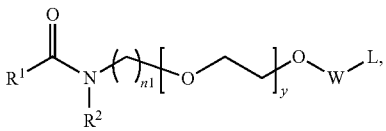

(Ia)

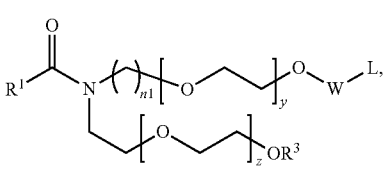

(Ib)

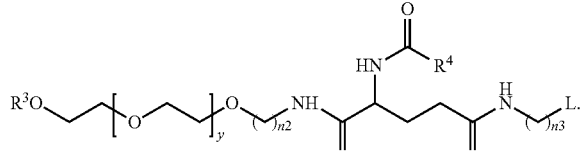

(Ic)

Another aspect of the present disclosure relates to a solid support comprising the compound of Formula (I) (including Formulas (Ia) through (Ic)) described herein covalently attached thereto. In some embodiments, the compound is covalent attached to the solid support via the $R^6$ group. In further embodiments, the solid support comprises controlled pore glass (CPG) support.

A further aspect of the present disclosure relates to a method of preparing a synthetic oligonucleotide or polynucleotide, comprising reacting a compound of Formula (I) (including Formulas (Ia) through (Ic)) described herein, with one or more nucleoside analogs, or an oligonucleotide or polynucleotide.

DETAILED DESCRIPTION

Figure 1:
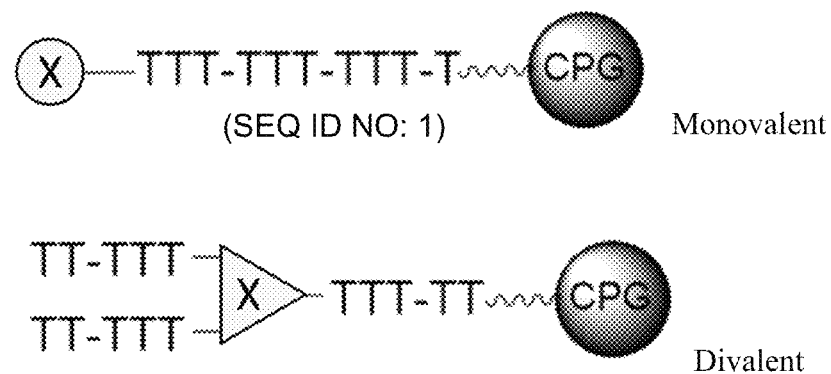
FIG. 1 depicts an oligonucleotide sequence coupled with monovalent and divalent lipid-PEG phosphoramidites according to certain embodiments of the present disclosure.

The present application discloses preparation of lipid-PEGylated solid support as well as lipid-PEGylated phosphoramidites for use to synthesize LONs under both pre-synthetic and post-synthetic approaches. In particular, the lipid moiety may contain fatty acid moieties, which may provide improved drug distribution after injection than cholesterol and tocopherol-conjugated siRNA.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, common organic abbreviations are defined as follows:
CBz benzyloxycarbonyl
bis-CEP bis(N,N-diisopropyl)-(2-cyanoethyl)phosphoramidite
CPG controlled pore glass
DEAD diethyl azodicarboxylate
DMTr 4, 4'-dimethoxytrityl
HATU 1-[bis(dimethylamino)methylene]-1H-1,2,3 -triazolo [4,5-b]pyridinium 3-oxid hexafluorophosphate
LCAA long chain alkylamine
PEG polyethylene glycol
Pfp perfluorophenyl
RT or rt room temperature
siRNA small-interfering RNA
TB TU 2-(1H-benzotriazol-1-yl)-1,1,3,3-tetramethylaminium tetrafluoroborate As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

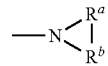

Whenever a group is described as being "optionally substituted" that group may be unsubstituted or substituted with one or more of the indicated substituents. Likewise, when a group is described as being "substituted", the substituent may be selected from one or more of the indicated substituents. If no substituents are indicated, it is meant that the indicated "optionally substituted" or "substituted" group may be one or more group(s) individually and independently selected from alkyl (e.g., $C_{1-6}$ alkyl); alkenyl (e.g., $C_{2-6}$ alkenyl); alkynyl (e.g., $C_{2-6}$ alkynyl); $C_{3-8}$ carbocyclyl (for example, $C_{3-8}$ cycloalkyl, $C_{3-8}$ cycloalkenyl, or $C_{3-8}$ cycloalkynyl, each may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_{1-6}$ alkoxy)$C_{1-6}$ alkyl); ($C_3$-$C_7$ carbocyclyl)$C_{1-6}$ alkyl (may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_{1-6}$ alkoxy)$C_{1-6}$ alkyl); 5-10 membered heterocyclyl (may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_{1-6}$ alkoxy)$C_{1-6}$ alkyl); (5-10 membered heterocyclyl)$C_{1-6}$ alkyl (may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_1$-$C_6$ alkoxy)$C_{1-6}$ alkyl); aryl (may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_{1-6}$ alkoxy)$C_{1-6}$ alkyl); (aryl)$C_{1-6}$ alkyl (may further be optionally substituted, for example, with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_1$-$C_6$ alkoxy)$C_{1-6}$ alkyl); 5-10 membered heteroaryl (may further be optionally substituted with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_1$-$C_6$ alkoxy)$C_{1-6}$ alkyl); (5-10 membered heteroaryl)$C_{1-6}$ alkyl (may further be optionally substituted with halo, $C_{1-6}$ alkyl, $C_{1-6}$ alkoxy, $C_{1-6}$ haloalkyl, $C_{1-6}$ haloalkoxy, $(C_{1-6}$ alkoxy$)C_{1-6}$ alkyl, or —O($C_{1-6}$ alkoxy)$C_{1-6}$ alkyl); halo (e.g., fluoro, chloro, bromo, iodo); cyano; hydroxy; protected hydroxy; alkoxy (e.g., $C_{1-6}$ alkoxy); haloalkyl (e.g., $C_{1-6}$ haloalkyl, such as —$CF_3$); haloalkyl (e.g., $C_{1-6}$ haloalkoxy such as —$OCF_3$); ($C_{1-6}$ alkoxy)$C_{1-6}$ alkyl; —O ($C_{1-6}$ alkoxy)$C_{1-6}$ alkyl; ($C_{1-6}$ haloalkoxy)$C_{1-6}$ alkyl; —O($C_{1-6}$ halo alkoxy)$C_{1-6}$ alkyl; aryloxy; sulfhydryl (mercapto); alkylthio (e.g., $C_{1-6}$ alkylthio); arylthio; azido; nitro; O-carbamyl; N-carbamyl; O-thiocarbamyl; N-thiocarbamyl; C-amido; N-amido; S-sulfonamido; N-sulfonamido; C-carboxy; protected C-carboxy; O-carboxy; acyl; cyanate; isocyanato; thiocyanato; isothiocyanato; silyl; sulfenyl; sulfinyl; sulfonyl; trihalomethanesulfonyl; trihalomethanesulfonamido; amino (including protected derivatives thereof); mono-substituted amino (for example, $NH(C_1$-$C_6$ alkyl); di-substituted amino (for example, $N(C_{1-6}$ alkyl)$_2$); oxo (=O); and thioxo (=S).

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl, aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_{1-6}$ alkyl includes $C_1$, $C_2$, $C_3$, $C_4$, $C_5$ and $C_6$ alkyl, $C_{2-6}$ alkyl, $C_1$-$C_3$ alkyl, etc. Similarly, $C_{3-8}$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

As used herein, "alkenyl" refers to a straight or branched hydrocarbon chain containing one or more double bonds. The alkenyl group may have 2 to 30 carbon atoms. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. The alkenyl group may be substituted or unsubstituted.

As used herein, "alkynyl" refers to a straight or branched hydrocarbon chain containing one or more triple bonds. The alkynyl group may have 2 to 30 carbon atoms. By way of example only, "$C_2$-$C_4$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like. The alkynyl group may be substituted or unsubstituted.

As used herein, "cycloalkyl" refers to a completely saturated (no double or triple bonds) mono- or multi- cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro [4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro [3.3]heptane, 2-oxa-6-azaspiro [3.3]heptane, 2,6-diazaspiro [3.3]heptane, 2-oxaspiro [3.4]octane and 2-azaspiro [3.4]octane.

As used herein, "alkylene" refers to a branched, or straight chain fully saturated di-radical chemical group containing only carbon and hydrogen that is attached to the rest of the molecule via two points of attachment. By way of example only, "$C_1$-$C_{10}$ alkylene" indicates that there are one to ten carbon atoms in the alkylene chain. Non-limiting examples include ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "alkenylene" refers to a straight or branched chain di-radical chemical group containing only carbon and hydrogen and containing at least one carbon-carbon double bond that is attached to the rest of the molecule via two points of attachment. The alkenylene group may be designated as "$C_2$-$C_{10}$ alkenylene" or similar designations. By way of example only, "$C_2$-$C_{10}$ alkenylene" indicates that there are two to ten carbon atoms in the alkenylene chain.

As used herein, "alkynylene" refers to a straight or branched chain di-radical chemical group containing only carbon and hydrogen and containing at least one carbon-carbon triple bond that is attached to the rest of the molecule via two points of attachment. The alkynylene group may be designated as "$C_2$-$C_{10}$ alkenylene" or similar designations. By way of example only, "$C_2$-$C_{10}$ alkynylene" indicates that there are two to ten carbon atoms in the alkynylene chain.

As used herein, "heteroalkylene" refers to an alkylene group, as defined herein, containing one or more heteroatoms in the carbon back bone (i.e., an alkylene group in which one or more carbon atoms is replaced with a heteroatom, for example, nitrogen atom, oxygen atom or sulfur atom). For example, a —$CH_2$— may be replaced with —O—, —S—, or —NH—. Heteroalkylene groups include, but are not limited to ether, thioether, amino-alkylene, and alkylene-amino-alkylene moieties. In some embodiments, the heteroalkylene may include one, two, three, four, or five —$CH_2CH_2O$— unit(s). Alternatively and/or additionally, one or more carbon atoms can also be substituted with an oxo (=O) to become a carbonyl. For example, a —$CH_2$— may be replaced with —C(=O)—.

As used herein, "aralkyl" and "(aryl)alkyl" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl. In some embodiments, the alkylene is an unsubstituted straight chain containing 1, 2, 3, 4, 5, or 6 methylene unit(s).

As used herein, "heteroaralkyl" and "(heteroaryl)alkyl" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs. In some embodiments, the alkylene is an unsubstituted straight chain containing 1, 2, 3, 4, 5, or 6 methylene unit(s).

As used herein, "(heterocyclyl)alkyl" refer to a heterocyclic or a heterocyclyl group, as defined above, connected, as a substituent, via an alkylene group, as defined above. The alkylene and heterocyclyl groups of a (heterocyclyl)alkyl may be substituted or unsubstituted. Examples include but are not limited to (tetrahydro-2H-pyran-4-yl)methyl, (piperidin-4-yl)ethyl, (piperidin-4-yl)propyl, (tetrahydro-2H-thiopyran-4-yl)methyl, and (1,3-thiazinan-4-yl)methyl. In some embodiments, the alkylene is an unsubstituted straight chain containing 1, 2, 3, 4, 5, or 6 methylene unit(s).

As used herein, "cycloalkylalkyl" and "(cycloalkyl)alkyl" refer to a cycloalkyl group (as defined herein) connected, as a substituent, via an alkylene group. Examples include but are not limited to cyclopropylmethyl, cyclobutylmethyl, cyclopentylethyl, and cyclohexylpropyl. In some embodiments, the alkylene is an unsubstituted straight chain containing 1, 2, 3, 4, 5, or 6 methylene unit(s).

As used herein, "alkoxy" refers to the formula —OR wherein R is an alkyl group, as defined herein. A non-limiting list of alkoxy group includes methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

As used herein, "amino" refer to a —$NH_2$ group. The term "mono-substituted amino group" as used herein refers to an amino (—$NH_2$) group where one of the hydrogen atom is replaced by a substituent. The term "di-substituted amino group" as used herein refers to an amino (—$NH_2$) group where each of the two hydrogen atoms is replaced by a substituent. The term "optionally substituted amino," as used herein refer to a —$NR_AR_B$ group where $R_A$ and $R_B$ are independently hydrogen, alkyl, cycloalkyl, aryl, heteroaryl, heterocyclyl, aralkyl, or heterocyclyl(alkyl), as defined herein.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups.

As used herein, "aminoalkyl" or "(amino)alkyl" refers to an alkyl group in which one or more of the hydrogen atoms are replaced by an amino group or "—$NR_AR_B$" group as defined herein. The alkyl portion of the aminoalkyl, includes, for example, $C_1$-$C_6$ alkyl.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

As used herein, "—O-alkoxyalkyl" or "—O-(alkoxy)alkyl" refers to an alkoxy group connected via an —O-(alkylene) group, such as —O-($C_{1-6}$ alkoxy)$C_1$-$C_6$ alkyl, for example, —O—$(CH_2)_{1-3}OCH_3$.

As used herein, "aryloxy" and "arylthio" refers to RO- and RS-, in which R is an aryl, as defined above, such as but not limited to phenyl. Both an aryloxy and arylthio may be substituted or unsubstituted.

A "sulfenyl" group refers to an "-SR" group in which R can be hydrogen, alkyl, alkenyl, alkynyl, carbocyclyl, aryl, heteroaryl, heterocyclyl, aralkyl, or heterocyclyl(alkyl), as defined above. A sulfenyl may be substituted or unsubstituted.

A "sulfinyl" group refers to an "—S(=O)-R" group in which R can be the same as defined with respect to sulfenyl. A sulfinyl may be substituted or unsubstituted.

A "sulfonyl" group refers to an "$SO_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, carbocyclyl, aryl, heteroaryl, heterocyclyl, aralkyl, or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester or C-carboxy may be substituted or unsubstituted.

A "trihalomethanesulfonyl" group refers to an "$X_3CSO_2$—"group wherein X is a halogen.

A "trihalomethanesulfonamido" group refers to an "$X_3CS(O)_2N(R)$—" group wherein X is a halogen and R is hydrogen, alkyl, alkenyl, alkynyl, carbocyclyl, aryl, heteroaryl, heterocyclyl, aralkyl, or heterocyclyl(alkyl), as defined herein.

A "mercapto" group refers to an "—SH" group.

An "S-sulfonamido" group refers to a "—$SO_2N(R_AR_B)$" group in which $R_A$ and $R_B$ can be independently hydrogen, alkyl, alkenyl, alkynyl, carbocyclyl, aryl, heteroaryl, heterocyclyl, aralkyl, or heterocyclyl(alkyl) as defined herein. An S-sulfonamido may be substituted or unsubstituted.

An "N-sulfonamido" group refers to a "$RSO_2N(R_A)$-" group in which R and $R_A$ can be independently hydrogen, alkyl, alkenyl, alkynyl, carbocyclyl, aryl, heteroaryl, heterocyclyl, aralkyl, or heterocyclyl(alkyl), as defined herein. An N-sulfonamido may be substituted or unsubstituted.

An "O-carbamyl" group refers to a "—OC(=O)N($R_AR_B$)" group in which $R_A$ and $R_B$ can be the same as defined with respect to S-sulfonamido. An O-carbamyl may be substituted or unsubstituted.

An "N-carbamyl" group refers to an "ROC(=O)N($R_A$)-" group in which R and $R_A$ can be the same as defined with respect to N-sulfonamido. An N-carbamyl may be substituted or unsubstituted.

An "O-thiocarbamyl" group refers to a "—OC(=S)-N($R_AR_B$)" group in which $R_A$ and $R_B$ can be the same as defined with respect to S-sulfonamido. An O-thiocarbamyl may be substituted or unsubstituted.

An "N-thiocarbamyl" group refers to an "ROC(=S)N($R_A$)-" group in which R and $R_A$ can be the same as defined with respect to N-sulfonamido. An N-thiocarbamyl may be substituted or unsubstituted.

A "C-amido" group refers to a "—C(=O)N($R_AR_B$)" group in which $R_A$ and $R_B$ can be the same as defined with respect to S-sulfonamido. A C-amido may be substituted or unsubstituted.

An "N-amido" group refers to a "RC(=O)N($R_A$)-" group in which R and $R_A$ can be the same as defined with respect to N-sulfonamido. An N-amido may be substituted or unsubstituted.

Where the numbers of substituents are not specified (e.g., haloalkyl), there may be one or more substituents present. For example, "haloalkyl" may include one or more of the same or different halogens.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition, it is understood that in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns. Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as —AE— or

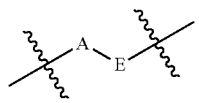

includes the substituent being oriented such that the A is attached at the leftmost attachment point of the molecule as well as the case in which A is attached at the rightmost attachment point of the molecule. In addition, if a group or substituent is depicted as

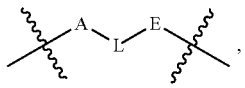

and when L is defined as a bond or absent; such group or substituent is equivalent to

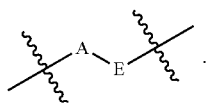

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, crystalline forms, amorphous form, solvated forms, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl (Bn); substituted benzyl; alkylcarbonyls (e.g., t-butoxycarbonyl (BOC), acetyl (i.e., —C(=O)CH$_3$ or Ac), or isobutyryl (iBu); arylalkylcarbonyls (e.g., benzyloxycarbonyl or benzoyl (i.e., —C(=O)Ph or Bz)); substituted methyl ether (e.g., methoxymethyl ether (MOM)); substituted ethyl ether (e.g., methoxyethyl ether (MOE); a substituted benzyl ether; tetrahydropyranyl ether; silyl ethers (e.g., trimethylsilyl (TMS), triethylsilyl, triisopropylsilyl, t-butyldimethylsilyl (TBDMS), tri-iso-propylsilyloxymethyl (TOM), or t-butyldiphenylsilyl); esters (e.g., benzoate ester); carbonates (e.g., methoxymethylcarbonate);

sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

Examples of hydroxy protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoro-acetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, $5^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl) amine, cyclohexylamine, dicyclohexylamine, triethanolamine, triethylamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like. In some embodiments, the compounds described herein may be in the form of a triethylamine salt.

As used herein, a "nucleotide" includes a nitrogen containing heterocyclic base, a sugar, and one or more phosphate groups. They are monomeric units of a nucleic acid sequence. In RNA, the sugar is a ribose, and in DNA a deoxyribose, i.e. a sugar lacking a hydroxyl group that is present in ribose. The nitrogen containing heterocyclic base can be purine or pyrimidine base. Purine bases include adenine (A) and guanine (G), and modified derivatives or analogs thereof, such as deazapurine. Pyrimidine bases include cytosine (C), thymine (T), and uracil (U), and modified derivatives or analogs thereof. The C-1 atom of deoxyribose is bonded to N-1 of a pyrimidine or N-9 of a purine.

As used herein, a "nucleoside" is structurally similar to a nucleotide, but is missing the phosphate moieties. An example of a nucleoside analogue would be one in which the label is linked to the base and there is no phosphate group attached to the sugar molecule. The term "nucleoside" is used herein in its ordinary sense as understood by those skilled in the art. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, deazapurine, 7-deazapurine, adenine, 7-deaza adenine, guanine, 7-deaza guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

As used herein, when an oligonucleotide is described as "comprising" or "incorporating" a nucleoside compound described herein, it means that the nucleoside described herein forms a covalent bond with the oligonucleotide. In some embodiments, the covalent bond is formed by the reaction of the 5' hydroxy group of the nucleoside of Formula (I) as described herein and the 3' phosphoramidite group of another nucleoside (which may be the terminal nucleoside of an oligonucleoside) to form a phosphodiester bond, or the reaction of the 3' phosphoramidite group of the nucleoside of Formula (I) as described herein with the 5' hydroxy group of another nucleoside (which may be the terminal nucleoside of an oligonucleoside) to form a phosphodiester bond or an equivalent thereof (e.g., thiophosphodiester).

As used herein, "derivative" or "analogue" means a synthetic nucleoside or nucleotide derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkyl-phosphonate, phosphoranilidate, phosphoramidite, and phosphoramidate linkages. "Derivative" and "analog" as used herein, may be used interchangeably, and are encompassed by the terms "nucleotide" and "nucleoside" defined herein.

As used herein, the term "phosphate" is used in its ordinary sense as understood by those skilled in the art, and includes its protonated forms (for example,

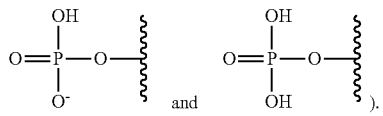

As used herein, the terms "monophosphate," "diphosphate," and "triphosphate" are used in their ordinary sense as understood by those skilled in the art, and include protonated forms.

Lipid PEGylated Compounds of Formula (I)

Some embodiments of the present disclosure relate to a compound of Formula (I):

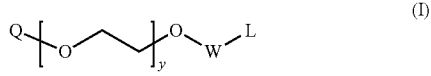

wherein Q is

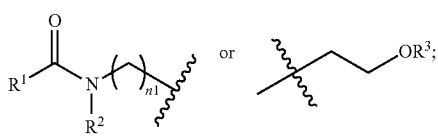

W is $C_1$-10 alkylene, 2 to 10 membered heteroalkylene, or

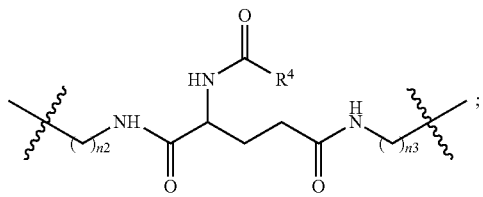

L is

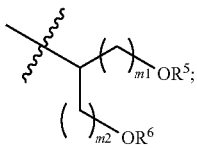

each of $R^1$ and $R^4$ is independently $C_{1-22}$ alkyl or $C_{2-22}$ alkenyl;

$R^2$ is H, $C_{1-6}$ alkyl or

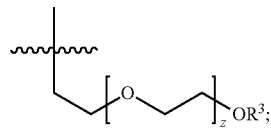

each of $R^3$ and $R^5$ is independently H or a hydroxyl protecting group;

$R^6$ is hydrogen, a phosphoramidite moiety, —C(=O)CH$_2$CH$_2$C(=O)R$^{6A}$, or —P(OR$^{6B}$)NR$^{6C}$R$^{6D}$;

$R^{6A}$ is —OH, —OR$^7$ or —NR$^8$R$^9$;

each of $R^{6B}$, $R^{6C}$ and $R^{6D}$ is independently H, $C_{1-6}$ haloalkyl, or optionally substituted $C_{1-6}$ alkyl;

$R^7$ is optionally substituted $C_{1-6}$ alkyl or a hydroxy protecting group; and each of $R^8$ and $R^9$ is independently H, optionally substituted $C_{1-6}$ alkyl or an amino protecting group;

each of y and z is independently an integer of 1 to 100;

each of n1, n2 and n3 is independently an integer of 1 to 10; and each of m1 and m2 is independently 0, 1, 2 or 3.

In some embodiments of the compounds of Formula (I), when Q is

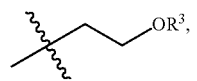

then W is

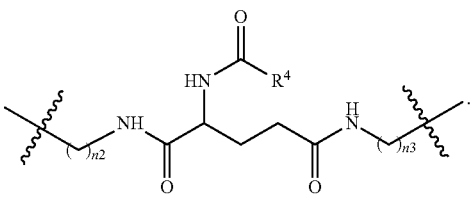

In some embodiments of the compounds of Formula (I), Q is

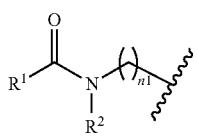

and the compounds have the structure of Formula (Ia):

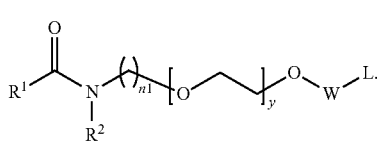

In some such embodiments, $R^1$ is $C_{1-22}$ alkyl, $C_{5-21}$ alkyl, $C_{7-19}$ alkyl, $C_{9-17}$ alkyl, or $C_{13-15}$ alkyl, such as $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$ or $C_{21}$ alkyl. In other embodiments, $R^1$ is $C_{2-22}$ alkenyl, $C_{5-21}$ alkenyl, $C_{7-21}$ alkenyl, $C_{9-19}$ alkenyl, $C_{11-17}$ alkenyl, or $C_{13-15}$ alkenyl, such as $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$ or $C_{21}$ alkenyl. In some such embodiments, $R^1$ is

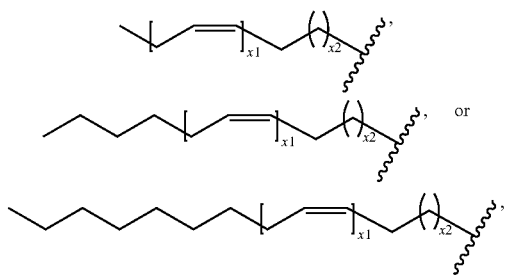

wherein each of x1 and x2 is independently an integer of 1 to 6. In some such embodiments, x1 is 2, 3, 4, 5 or 6. In one embodiment, $R^1$ is

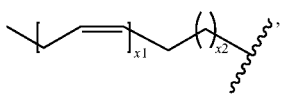

wherein x1 is 3 and x2 is 6. In one embodiment, $R^1$ is

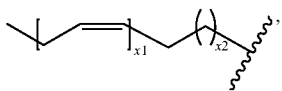

wherein x1 is 5 and x2 is 2. In one embodiment, $R^1$ is

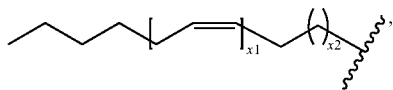

wherein x1 is 6 and x2 is 1. In another embodiment, $R^1$ is and wherein x1 is 2 and x2 is 6. In another embodiment, $R^1$ is

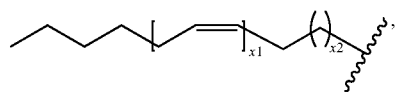

wherein x1 is 4 and x2 is 2. In yet another embodiment, $R^1$ is

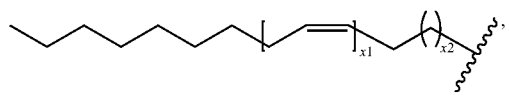

wherein x1 is 1 and x2 is 6.

In some embodiments of the compounds of Formula (I) or (Ia), $R^2$ is H. In further embodiments, n1 is 2 or 3. In other embodiments, $R^2$ is

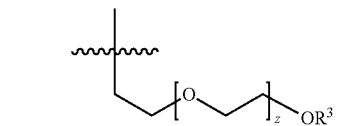

and the compound have the structure of Formula (Ib):

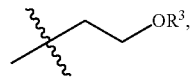

In some embodiments, z is an integer of 1, 2, 3, 4, 5, 6, 7, 8, 9, 10, 11, 12, 13, 14, 15, 16, 17, 10, 19, 20, or a range defined by any two of the preceding values. In further embodiments, z is from 1 to 10, from 2 to 9, from 3 to 8, from 4 to 7 or from 2 to 7. In some embodiments, y is an integer of 1, 2, 3, 4, 5, 6, 7, 8, 9, 10, 11, 12, 13, 14, 15, 16, 17, 10, 19, 20, or a range defined by any two of the preceding values. In further embodiments, y is from 1 to 10, from 2 to 9, from 3 to 8, from 4 to 7 or from 2 to 7.

In some embodiments of the compounds of Formula (I), (Ia) or (Ib), W is —$CH_2$—.

In some other embodiments of the compounds of Formula (I), Q is

W is

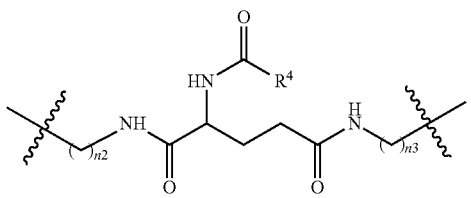

and the compounds have the structure of Formula (Ic):

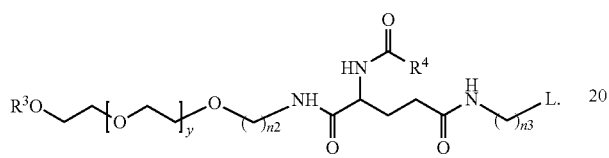

(Ic)

In some such embodiment, n3 is 1, 2, 3, 4, 5 or 6. In one embodiment, n3 is 4 and W is

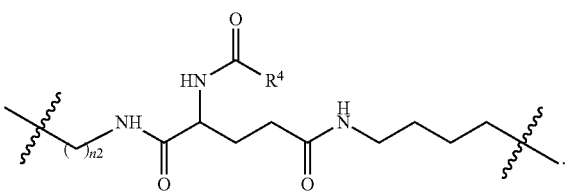

In some further embodiments, n2 is 1, 2 or 3. In some embodiments, y is an integer of 1, 2, 3, 4, 5, 6, 7, 8, 9, 10, 11, 12, 13, 14, 15, 16, 17, 10, 19, 20, or a range defined by any two of the preceding values. In further embodiments, y is from 1 to 10, from 2 to 9, from 3 to 8, from 4 to 7 or from 2 to 7. In some such embodiments, $R^4$ is $C_{1-22}$ alkyl, $C_{5-21}$ alkyl, $C_{7-19}$ alkyl, $C_{9-17}$ alkyl, or $C_{13-15}$ alkyl, such as $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$ or $C_{21}$ alkyl. In other embodiments, $R^4$ is $C_{2-22}$ alkenyl, $C_{5-21}$ alkenyl, $C_{7-21}$ alkenyl, $C_{9-19}$ alkenyl, $C_{11-17}$ alkenyl, or $C_{13-15}$ alkenyl, such as $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$ or C21 alkenyl. In some further embodiments, $R^4$ is

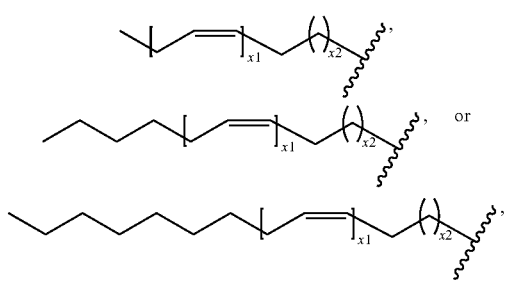

wherein each of x1 and x2 is independently an integer of 1 to 6. In some such embodiments, xis 2, 3, 4, 5 or 6. In one embodiment, $R^4$ is

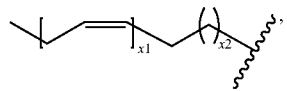

wherein x1 is 3 and x2 is 6. In one embodiment, $R^4$ is

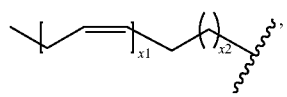

wherein x1 is 5 and x2 is 2. In one embodiment, $R^4$ is

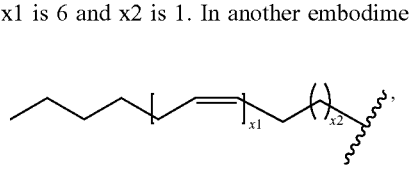

wherein x1 is 6 and x2 is 1. In another embodiment, $R^4$ is

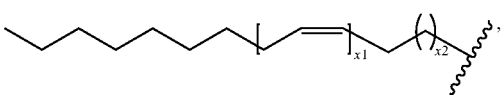

and wherein x1 is 2 and x2 is 6. In another embodiment, $R^4$ is

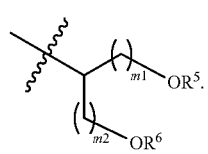

wherein x1 is 4 and x2 is 2. In yet another embodiment, $R^4$ is wherein x1 is 1 and x2 is 6.

In some embodiments of the compounds of Formula (I), (Ia), (Ib) or (Ic), $R^3$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl and 9-(4-methoxyphenyl)xanthen-9-yl. In one embodiment, R3 is bis(4-methoxyphenyl)phenylmethyl (DMT or DMTr).

In any embodiments of the compounds of Formula (I), (Ia), (Ib) or (Ic), L is

In some such embodiments, both m1 and m2 are 1, and L is

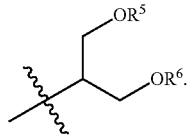

In other embodiments, m1 is 0 and m2 is 1, and L is

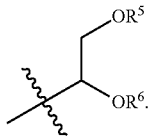

In other embodiments, m1 is 1 and m2 is 0. In other embodiments, m1 is 2 and m2 is 1. In other embodiments, m1 is 1 and m2 is 2. In other embodiments, both m1 and m2 are 2. In some embodiments, $R^5$ is H. In some other embodiments, $R^5$ is a trityl type of hydroxy protecting group selected from the group consisting of (4-methoxyphenyl) diphenylmethyl, bis(4-methoxyphenyl)phenylmethyl, tris (4-methoxyphenyl)methyl, 9-phenylxanthen-9-yl and 9-(4-methoxyphenyl)xanthen-9-yl. In one embodiment, $R^5$ is DMT. In some such embodiments, $R^6$ is -C(=O)CH$_2$CH$_2$C(=O)OH. In other embodiments, $R^6$ is

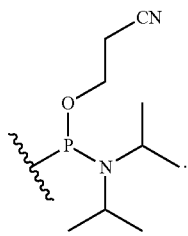 [SMILES: *P(OCCC#N)N(C(C)C)C(C)C]

In this case, the compound may be used for conjugating to an oligonucleotide/polynucleotide, as the compound may react with 3' or 5' terminal of an oligonucleotide/polynucleotide via standard phosphoramidite chemistry. In further embodiment, the oligonucleotide/polynucleotide is a double-stranded RNA, such as siRNA. In some such embodiments, the lipid conjugate is formed at the 3' end of the sense strand or the 3' end of the antisense strand.

In any embodiments of the compounds of Formula (I), (Ia), (Ib) or (Ic), each of y and z is independently an integer from 1 to 100, 1 to 50, 1 to 40, 1 to 30, or 1 to 20. For example, each of y and z is an integer of 1, 2, 3, 4, 5, 6, 7, 8, 9, 10, 11, 12, 13, 14, 15, 16, 17, 10, 19, 20, 21, 22, 23, 24, 25, 26, 27, 28, 29, 30, or a range defined by any two of the preceding values. In further embodiments, each of y and z is independently from 1 to 10, from 2 to 9, from 3 to 8, from 4 to 7, or from 2 to 7.

Additional non-limiting embodiments of the compounds of Formula (I) include:

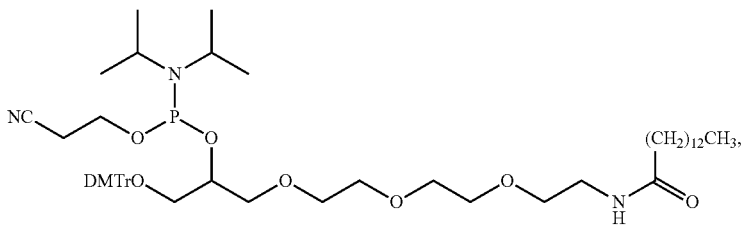

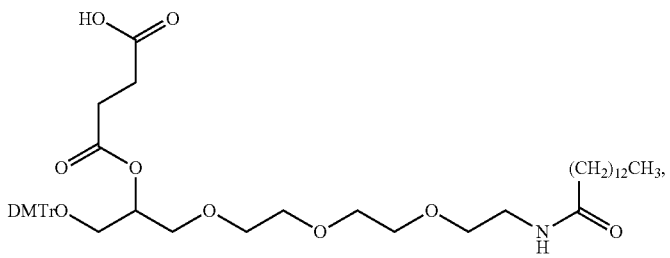

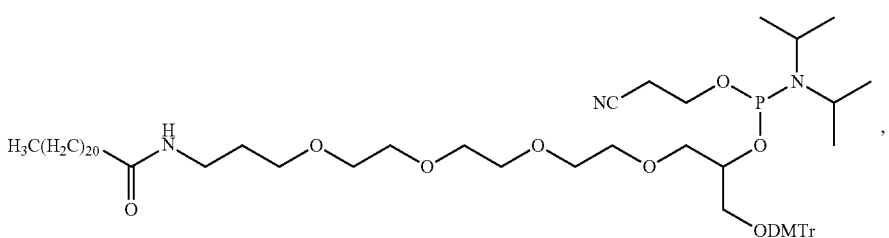

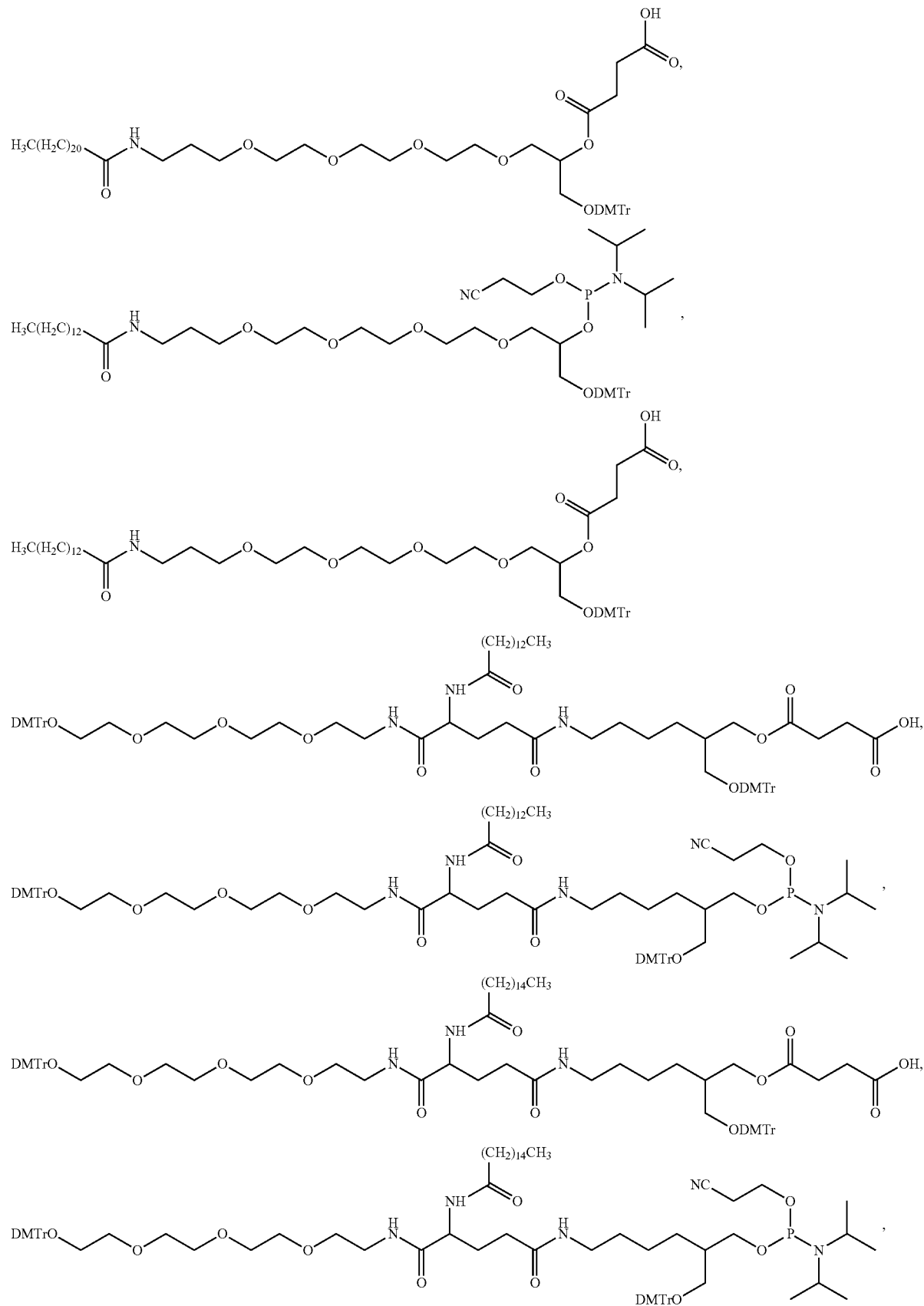

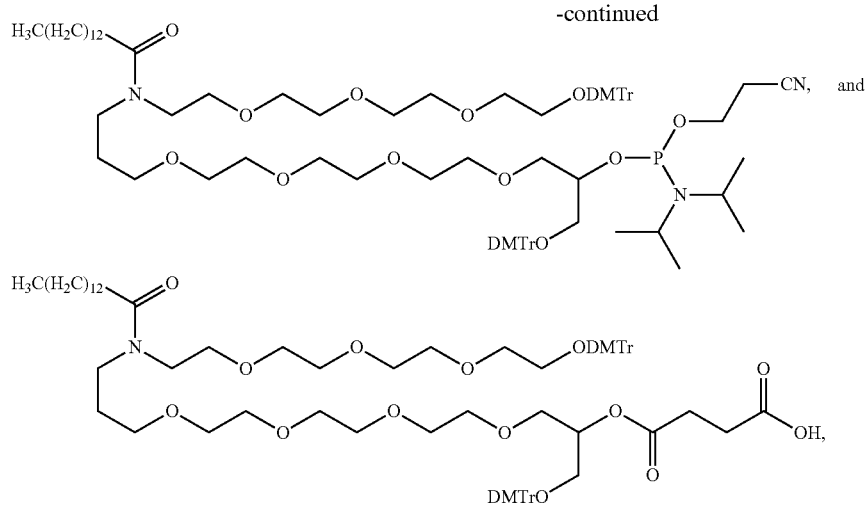

and pharmaceutically acceptable salts thereof. For example, the succinic acid (succinate) version of the compound may be in the form of a triethylamine salt.

Solid Support

Some embodiments of the present disclosure relate to a solid support comprising the lipid PEGylated compound of Formula (I) (including (Ia) through (Ic)) described herein covalently attached thereto. In some embodiments, the compound is covalently attached to the solid support via the $R^6$ group of the compound. In particular, the compound is covalently attached via a moiety:

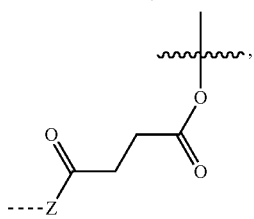

wherein Z is O or NH, and wherein the dashed line refers to the connection with the solid support, optionally through an additional linker, and wherein the squiggly line refers to the point of the attachment of the oxygen atom that is covalently attached to $R^6$ of the compound, to the remaining portion of the compound.

In some embodiments, the compound of Formula (I) is further incorporated into a nucleoside analog or an oligonucleotide sequence. The incorporation of the compound may be a reaction between a hydroxy group of the compound with the nucleoside or oligonucleoside. For example, via the —$OR^5$ moiety of the compound (after deprotecting of the hydroxy protecting group $R^5$), or via the —$OR^3$ moiety of the compound (after deprotecting of the hydroxy protecting group $R^3$), or both.

In any embodiments, the solid support may comprise controlled pore glass (CPG) support, or macroporous polystyrene (MPPS), or any other type of solid support that is appropriate for oligo synthesis.

Methods in Nucleoside or Oligonucleotide Synthesis

Some embodiments of the present application relate to a method for preparing a synthetic oligonucleotide or polynucleotide, comprising reacting a compound of Formula (I) (including Formulas (Ia) through (Ic)) described herein, with one or more nucleoside analogs, or an oligonucleotide or polynucleotide. In some embodiments, the oligonucleoside has 1 to 100 nucleobase lengths. In further embodiments, the oligonucleotide/polynucleotide comprises or is single-stranded RNA, double-stranded RNA, or siRNA. In further embodiments, the siRNA having a nucleobase length from about 10 to about 30. In further embodiments, the reaction is conducted on a solid support. In some such embodiments, the lipid conjugate is formed at the 3' end of the sense strand or the 3' end of the antisense strand.

A synthetic cycle of oligonucleotide using a nucleoside containing phosphoramidite moiety is described below in details.

Step 1: De-blocking (Detritylation)

The DMTr group is removed with a solution of an acid, such as 2% trichloroacetic acid (TCA) or 3% dichloroacetic acid (DCA), in an inert solvent (dichloromethane or toluene). The orange-colored DMTr cation formed is washed out; the step results in the solid support-bound oligonucleotide precursor bearing a free 5'-terminal hydroxy group.

Step 2: Coupling

A 0.02-0.2M solution of nucleoside phosphoramidite (or a mixture of several phosphoramidites) in acetonitrile is activated by a 0.2-0.7 M solution of an acidic azole catalyst, 1H-tetrazole, 5-ethylthio-1H-tetrazole, 2-benzylthiotetrazole, 4,5-dicyanoimidazole, or a number of similar compounds. The mixing is usually very brief and occurs in fluid lines of oligonucleotide synthesizers (see below) while the components are being delivered to the reactors containing solid support. The activated phosphoramidite in 1.5-20-fold excess over the support-bound material is then brought in contact with the starting solid support (first coupling) or a support-bound oligonucleotide precursor (following couplings) whose 5'-hydroxy group reacts with the activated phosphoramidite moiety of the incoming nucleoside phosphoramidite to form a phosphite triester linkage. The reaction is also highly sensitive to the presence of water, particularly when dilute solutions of phosphoramidites are used, and is commonly carried out in anhydrous acetonitrile. Upon the completion of the coupling, any unbound reagents and by-products are removed by washing.

Step 3: Capping

The capping step is performed by treating the solid support-bound material with a mixture of acetic anhydride and 1-methylimidazole or, less often, DMAP as catalysts and, in the phosphoramidite method, serves two purposes. After the completion of the coupling reaction, a small percentage of the solid support-bound 5'-OH groups (0.1 to 1%) remains unreacted and needs to be permanently blocked from further chain elongation to prevent the formation of oligonucleotides with an internal base deletion commonly referred to as (n-1) shortmers. The unreacted 5'-hydroxy groups are, to a large extent, acetylated by the capping mixture. It has also been reported that phosphoramidites activated with $^1$H-tetrazole react, to a small extent, with the $O^6$ position of guanosine. Upon oxidation with $I_2$/water, this side product, possibly via $O^6$-N7 migration, undergoes depurination. The apurinic sites thus formed are readily cleaved in the course of the final deprotection of the oligonucleotide under the basic conditions to give two shorter oligonucleotides thus reducing the yield of the full-length product. The $O^6$ modifications are rapidly removed by treatment with the capping reagent as long as the capping step is performed prior to oxidation with $I_2$/water.

Step 4: Oxidation

The newly formed tricoordinated phosphite triester linkage is not natural and is of limited stability under the conditions of oligonucleotide synthesis. The treatment of the support-bound material with iodine and water in the presence of a weak base (pyridine, lutidine, or collidine) oxidizes the phosphite triester into a tetracoordinated phosphate triester, a protected precursor of the naturally occurring phosphate diester internucleosidic linkage. Oxidation may be carried out under anhydrous conditions using tert-Butyl hydroperoxide or (1S)-(+)-(10-camphorsulfonyl)-oxaziridine (CSO). The step of oxidation may be substituted with a sulfurization step to obtain oligonucleotide phosphorothioates. In the latter case, the sulfurization step is best carried out prior to capping.

In solid-phase synthesis, an oligonucleotide being assembled is covalently bound, via its 3'-terminal hydroxy group, to a solid support material and remains attached to it over the entire course of the chain assembly. The solid support is contained in columns whose dimensions depend on the scale of synthesis and may vary between 0.05 mL and several liters. At the end of the chain assembly, the oligonucleotide is released from the solid support and is eluted from the column or the well. The two most often used solid-phase materials are controlled pore glass (CPG) and macroporous polystyrene (MPPS).

In contrast to organic solid-phase synthesis and peptide synthesis, the synthesis of oligonucleotides proceeds best on non-swellable or low-swellable solid supports. The two most often used solid-phase materials are controlled pore glass (CPG) and macroporous polystyrene (MPPS).

CPG is commonly defined by its pore size. In oligonucleotide chemistry, pore sizes of 500, 1000, 1500, 2000, and 3000 Å are used to allow the preparation of about 50, 80, 100, 150, and 200-mer oligonucleotides, respectively. To make native CPG suitable for further processing, the surface of the material is treated with (3-aminopropyl)triethoxysilane to give aminopropyl CPG. The aminopropyl arm may be further extended to result in long chain aminoalkyl (LCAA) CPG. The amino group is then used as an anchoring point for linkers suitable for oligonucleotide synthesis.

MPPS suitable for oligonucleotide synthesis is a low-swellable, highly cross-linked polystyrene obtained by polymerization of divinylbenzene, styrene, and 4-chloromethylstyrene in the presence of a porogeneous agent. The macroporous chloromethyl MPPS obtained is converted to aminomethyl MPPS.

EXAMPLES

Some aspects of the embodiments discussed above are disclosed in further detail in the following examples, which are not in any way intended to limit the scope of the present disclosure. Those in the art will appreciate that many other embodiments also fall within the scope of the compositions, kits and methods of the present application, as is described herein above and in the claims.

Example 1. Synthetic Routes to Prepare PEG Linkers

General Synthetic Route to Prepare a PEG Linker A

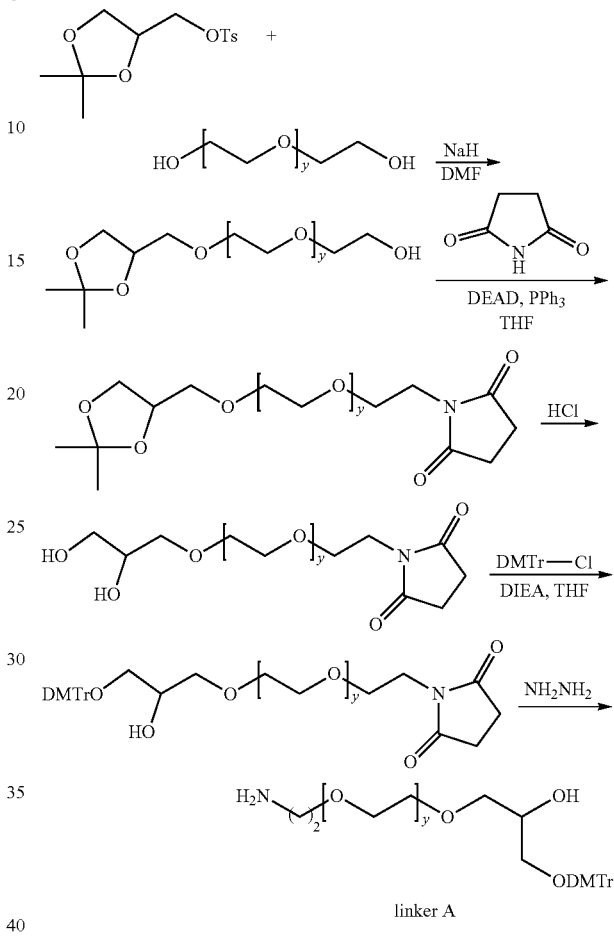

linker A

General Synthetic Route to Prepare a PEG Linker B

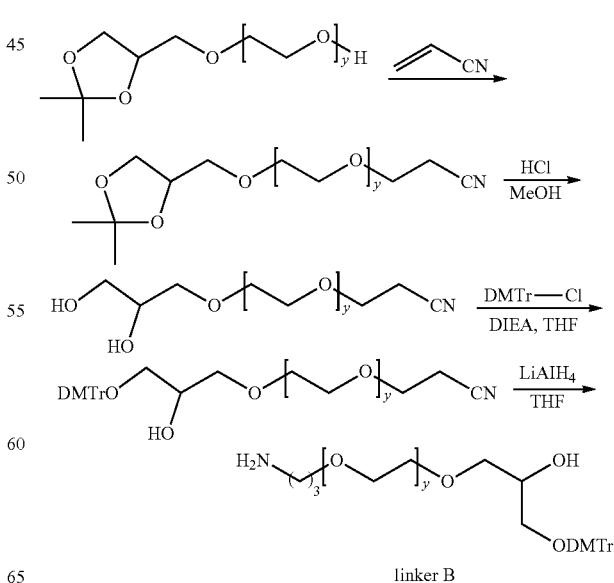

linker B

Scheme 1. Synthetic route to prepare PEG linker 1.5

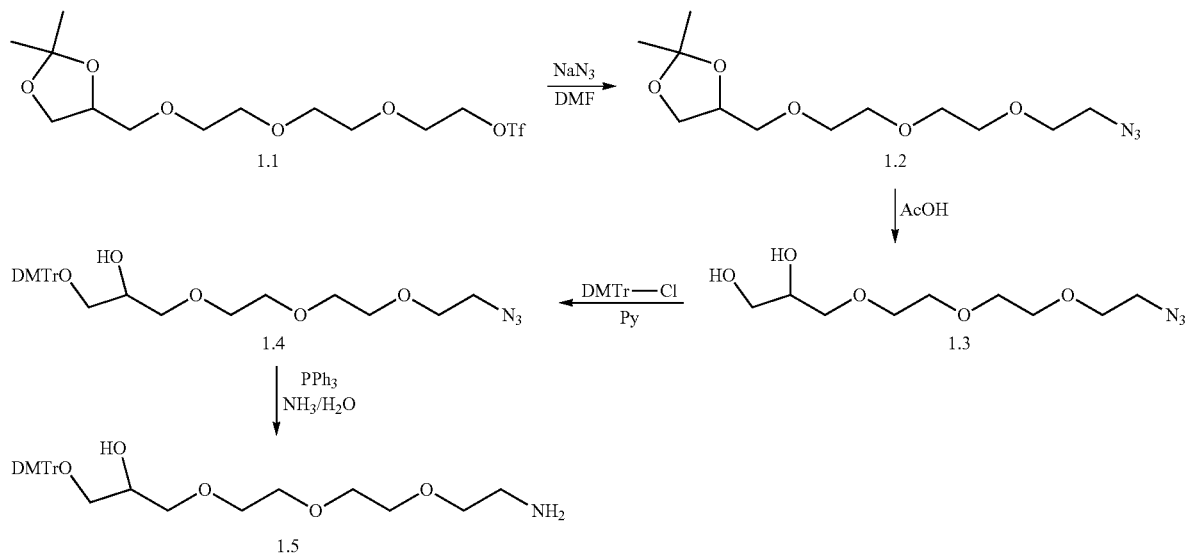

Compound 1.3: Compound 1.3 was synthesized as shown above according to the procedure in WO2015097262 A1.

Compound 1.4: Compound 1.3 (619 mg, 2.48 mmol) was dissolved in pyridine (15 mL) and DMTrCl (924 mg, 2.73 mmol) was then added. The reaction mixture was allowed to stir at room temperate (rt) overnight. The reaction was quenched with 5% $NaHCO_3$ solution and extracted with DCM (3×10 mL). The combined organic phases were dried over sodium sulfate, filtered, and concentrated to dryness. The crude material was then purified by column chromatography (0-10% MeOH in DCM) giving compound 1.4 as a white solid (913 mg, 66% yield). MS: found $[M+NH4]^+$=569.7; calc: $[M+NH4]^+$=569.3.

Compound 1.5: Compound 1.4 (913 mg, 1.65 mmol) from the previous step in pyridine (30 mL) was treated with PPh3 (447 mg, 1.82 mmol) for 12 h at rt. The reaction mixture was treated with concentrated aqueous $NH_3$ (5 mL) and stirred for a another 12 h. It was then concentrated under reduced pressure. The residue was dissolved in methanol (20 mL), washed with hexane (120 mL) and diluted with ethyl acetate (40 mL). The resulting solution was dried over $Na_2SO_4$ and concentrated in vacuo. The product was purified by column chromatography on silica gel to obtain compound 1.5 (432 mg, 49% yield). MS: found $[M+H]^+$=526.4; calc: $[M+H]^+$=526.3.

Example 2. Synthetic Routes to Prepare Lipid-PEGylated Compounds of Formula (Ia)

General Synthetic Route to Prepare a Compound of Formula (Ia)

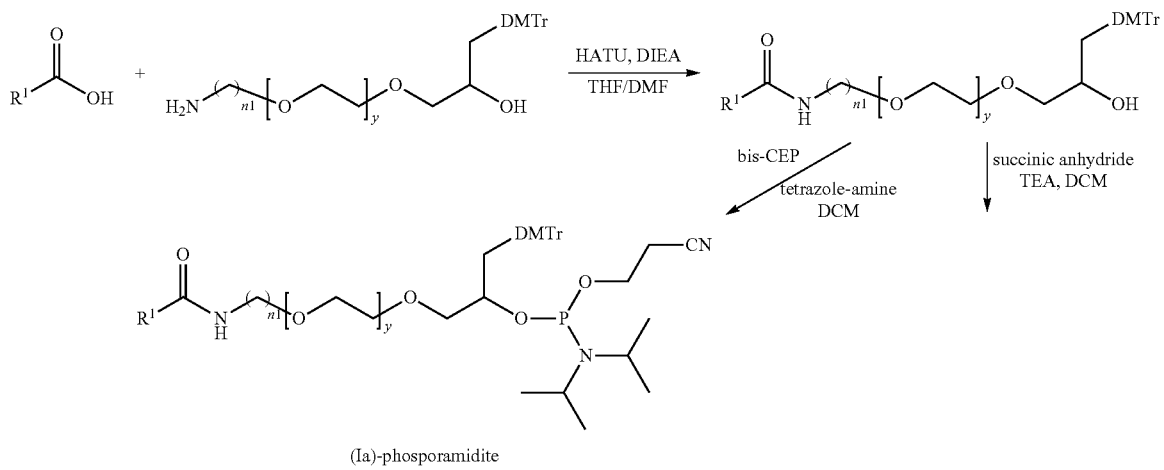

(Ia)-phosporamidite

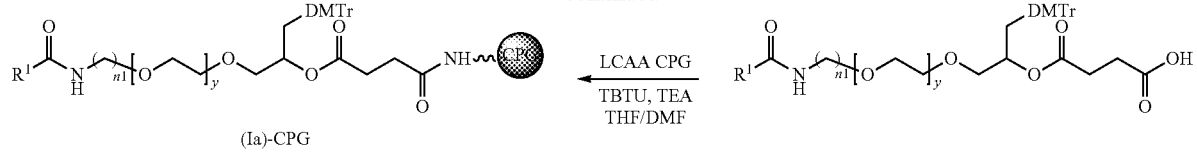
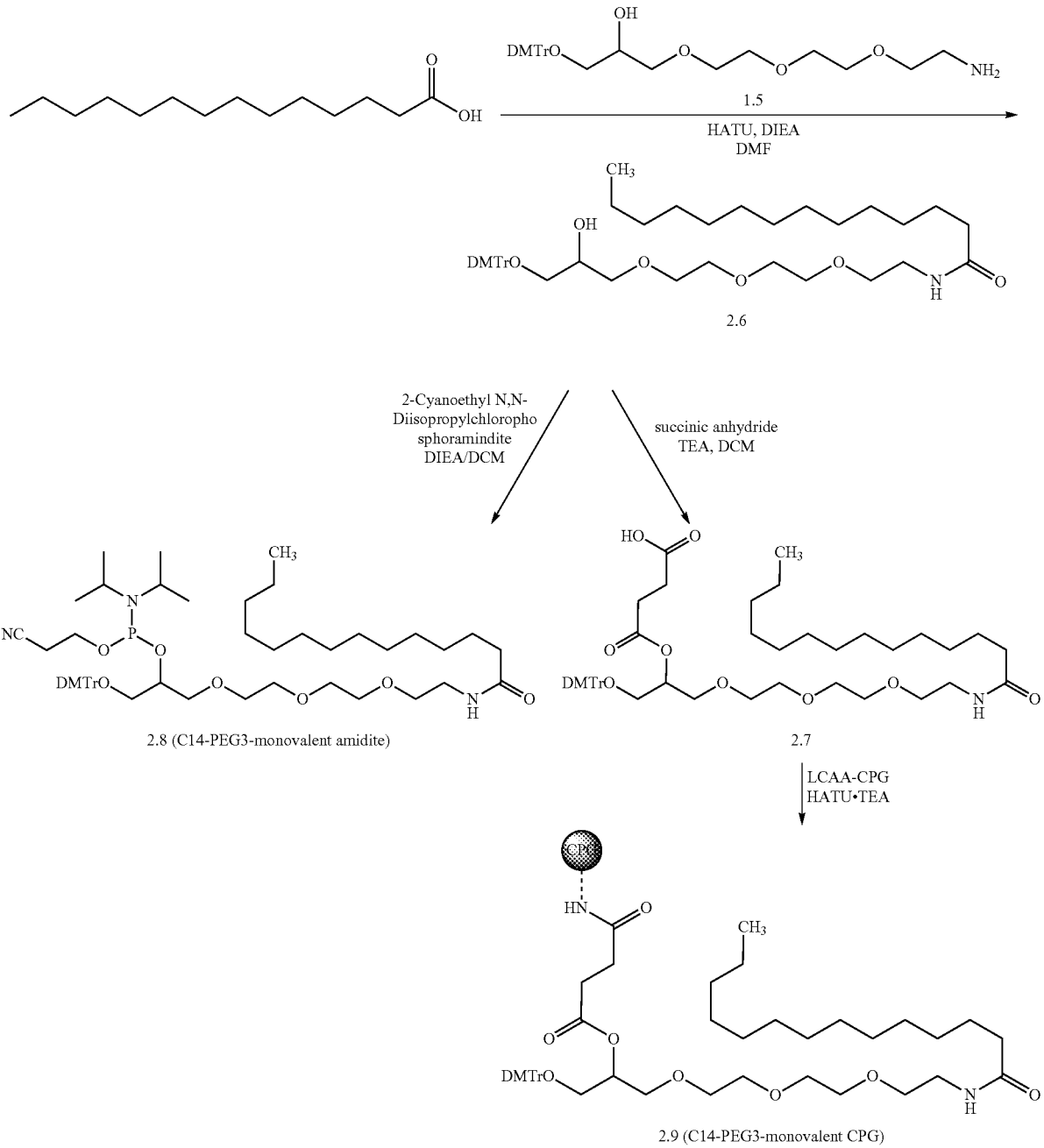
Compound 2.6: In a 100 mL RB flask, PEG linker compound 1.5 (432 mg, 0.82 mmol) was dissolved in DCM (50 mL). HATU (623 mg, 1.64 mmol), DIEA (423 mg, 3.28 mmol) and myristic acid (187 mg, 0.82 mmol) were then added. The reaction mixture was stirred for 4 h at rt. Completion of the reaction was confirmed by TLC. This mixture was then poured into saturated NaHCO₃ (50 mL) and extracted with DCM (30 mL). The organic layer was separated, washed with water, brine and dried over Na₂SO₄. After filtration, the organic layer was concentrated to dryness under vacuum. The crude product was purified by column purification using DCM/MeOH (0-10% MeOH). The pure fractions were collected and concentrated to dryness under vacuum to obtain compound 2.6 (0.53 g, 87%). MS: found: [M+NH4]⁺=753.9; calc: [M+NH4]⁺=753.5.

Compound 2.7: In a 25 mL RB flask, compound 2.6 (190 mg, 0.28 mmol) was dissolved in DCM (5 mL). Succinic anhydride (51.7 mg, 0.517 mmol) and TEA (103.4 mg, 1.304 mmol) were added. The reaction mixture was stirred at rt for 12 h. Completion of the reaction was confirmed by TLC. This mixture was then poured into saturated NaHCO₃ (20 mL) and extracted with DCM (30 mL). The organic layer was separated, washed with water, brine and dried over Na₂SO₄. After filtration, the organic layer was concentrated to dryness under vacuum. The crude product was purified by column purification using DCM/MeOH (0 to 10% MeOH). The pure fractions were collected and concentrated to dryness under vacuum to obtain compound 2.7 (80 mg, 34%). MS: found: [M–H]³¹ =834.9; calc: [M–H]⁻=834.5.

product was purified by column purification using DCM/TEA (0% to 10% TEA). The pure fractions were collected and concentrated to dryness under vacuum to obtain compound 2.8 (245 mg, 49%). MS: found: [M–H]⁺=936.7; calc: [M+H]⁺=936.6. ³¹PNMR (mixture of diastereomers, CDCl₃): δ 149.581, 149.084.

Compound 2.9 (C14-PEG3-monovalent-CPG): In a 25 mL RB flask, compound 2.7 (60 mg, 0.072 mmol) was dissolved in MeCN (10 mL). HATU (27.4 mg, 0.072 mmol) and DIEA (27.9 mg, 0.216 mmol) were added. After 5 min, LCAA CPG (2 g, 1000 Å) was added. The reaction mixture was stirred at rt for 3 h. After filtration, this GPG was washed with MeCN (50 mL×3) and THF (50 mL×3) and dried under vacuum. Cap A reagent: (THF/acetic anhydride/pyridine 80/10/10 v/v/v, 5 mL). and Cap B reagent: (1-methylimidazole/THF, 16/84, v/v, 5 mL) were added into the flask, and the mixture was stirred for 2 h at rt. After filtration, the capped GPG was washed with EtOH (50 mL×3), EtOH/Pyridine (10%) (50 mL×3), THF (50 mL×3) and DCM (50 mL×3). Compound 2.9 was then dried under vacuum. Loading was determined by standard DMTr assay by UV-Vis (498 nm) to be 48 μmol/g.

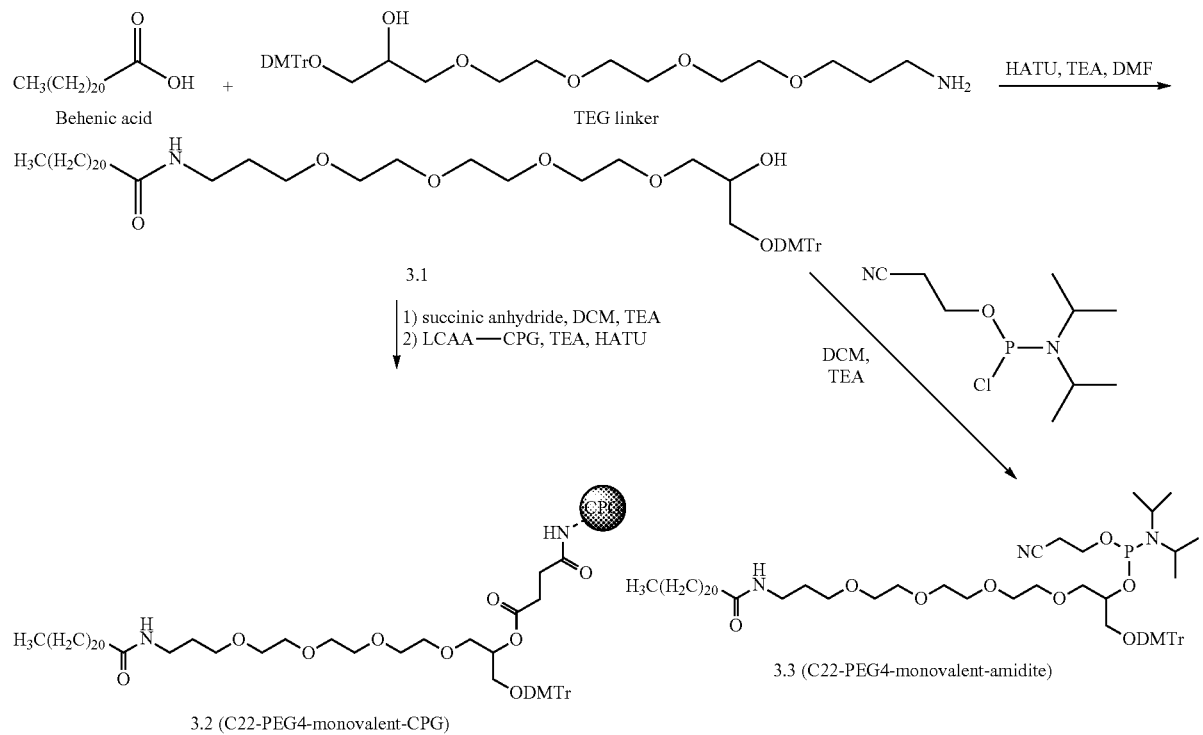

Compound 2.8 (C14-PEG3-monovalent-phosphoramidite): In a 50 mL RB flask, compound 2.6 (400 mg, 0.54 mmol) was dissolved in DCM (20 mL). 2-Cyanoethyl N,N-diisopropylchlorophosphoramidite (165 mg, 0.70 mmol) and DIEA (139 mg, 1.08 mmol) were added. The reaction mixture was stirred at rt for 2 h. Completion of the reaction was confirmed by TLC. This mixture was then poured into saturated NaHCO₃ (10 mL) and extracted with DCM (20 mL). The organic layer was separated, washed with water, brine and dried over Na₂SO₄. After filtration, the organic layer was concentrated to dryness under vacuum. The crude Compound 3.1: Behenic acid (0.149 g, 0.437 mmol) and TEG linker (0.28 g, 0.472 mmol) were dissolved in DMF (2.7 mL). HATU (0.20 g, 0.524 mol) was added followed by DIEA (0.15 mL, 0.874 mmol). The reaction mixture was stirred at rt for 3.5 h, and TLC confirmed reaction completion. The mixture was diluted with DCM (20 mL) and then poured into saturated NaHCO₃ solution (27 mL) with vigorous stifling. The organic phase was separated, and the aqueous phase was then extracted with DCM (20 mL×3). The combined organic phases were dried over Na₂SO₄, filtered, and concentrated to dryness. Crude product was purified by flash column eluted with 1% TEA in DCM : MeOH (0% to 5% MeOH) to obtain compound 3.1 (0.25 g, 63%). MS: found [M+ACOH−H]⁻=964.9; calc: [M+ACOH−H]−=964.6.

Compound 3.2 (C22-PEG4-monovalent-CPG): Step 1: Compound 3.1 (0.10 g, 0.110 mmol) was dissolved in DCM (0.55 mL) and succinic anhydride (16.5 mg, 0.165 mmol) was then added followed by TEA (31 µL, 0.220 mmol). The reaction mixture was allowed to stir at rt overnight, and TLC indicated reaction completion. Crude product was purified by flash column eluted with 1% TEA in DCM : MeOH (0% to 5% MeOH) to obtain the corresponding succinate as TEA salt (0.12 g, 98.4%). MS: found [M+NH4]⁺=1024.1; calc: [M+NH4]⁺=1024.4.

Step 2: In a 25 mL RB flask succinate from step 1 (0.12 g, 0.108 mmol) was dissolved in MeCN (8.0 mL). HATU (47 mg, 0.124 mmol) and DIEA (65 µL, 0.371 mmol) were added. After 5 min LCAA CPG (1.6 g, 500 Å) was added. The reaction mixture was rotated on a rotary evaporator at rt for 3 h. After filtration, this GPG was washed with MeCN (8 mL×3) and THF (8 mL×3) and dried under vacuum for 30 min. Loading was determined by standard DMTr assay by UV-Vis (498 nm) to be 50 µmol/g.

Capping: In a 25 mL RB flask THF (6.4 mL) was added to the uncapped CPG followed by pyridine (0.8 mL) and acetic anhydride (0.8 mL). The reaction was rotated on a rotary evaporator at rt for 15 min. The capped CPG was then filtered, washed with THF (8 mL), 10% pyridine in MeOH (8 ml×2), MeOH (8 mL), MeCN (8 mL×2), and DCM (8 mL). This capped CPG was dried under high vacuum for 30 min. Loading was determined by standard DMTr assay by UV-Vis (498 nm) to be 49 µmol/g. Ninhydrin test: negative.

Compound 3.3 (C22-PEG4-monovalent-phosphoramidite): Compound 3.1 (0.15 g, 0.166 mmol) was dissolved in DCM (8.3 mL). 2-Cyanoethyl N,N-diisopropylchlorophosphoramidite (55.4 µL, 0.248 mmol) and DIEA (86.7 µL, 0.498 mmol) were added. The reaction mixture was stirred at rt for 2 h. Completion of the reaction was confirmed by TLC. This mixture was then poured into saturated NaHCO₃ (20 mL) and extracted with DCM (20 mL×2). The combined organic layers were dried over MgSO₄, filtered, and concentrated to dryness. The crude product was purified by flash column chromatography using 2% TEA in hexanes/EtOAc (0 to 85% EtOAc). The pure fractions were collected and concentrated to dryness under vacuum to obtain compound 3.3 (220 mg). MS: found: [M+NH4]⁺=1124.1; calc: [M+NH4]⁺=1124.5. ³¹PNMR (mixture of diastereomers, CDCl₃): δ 149.734, 149.199.

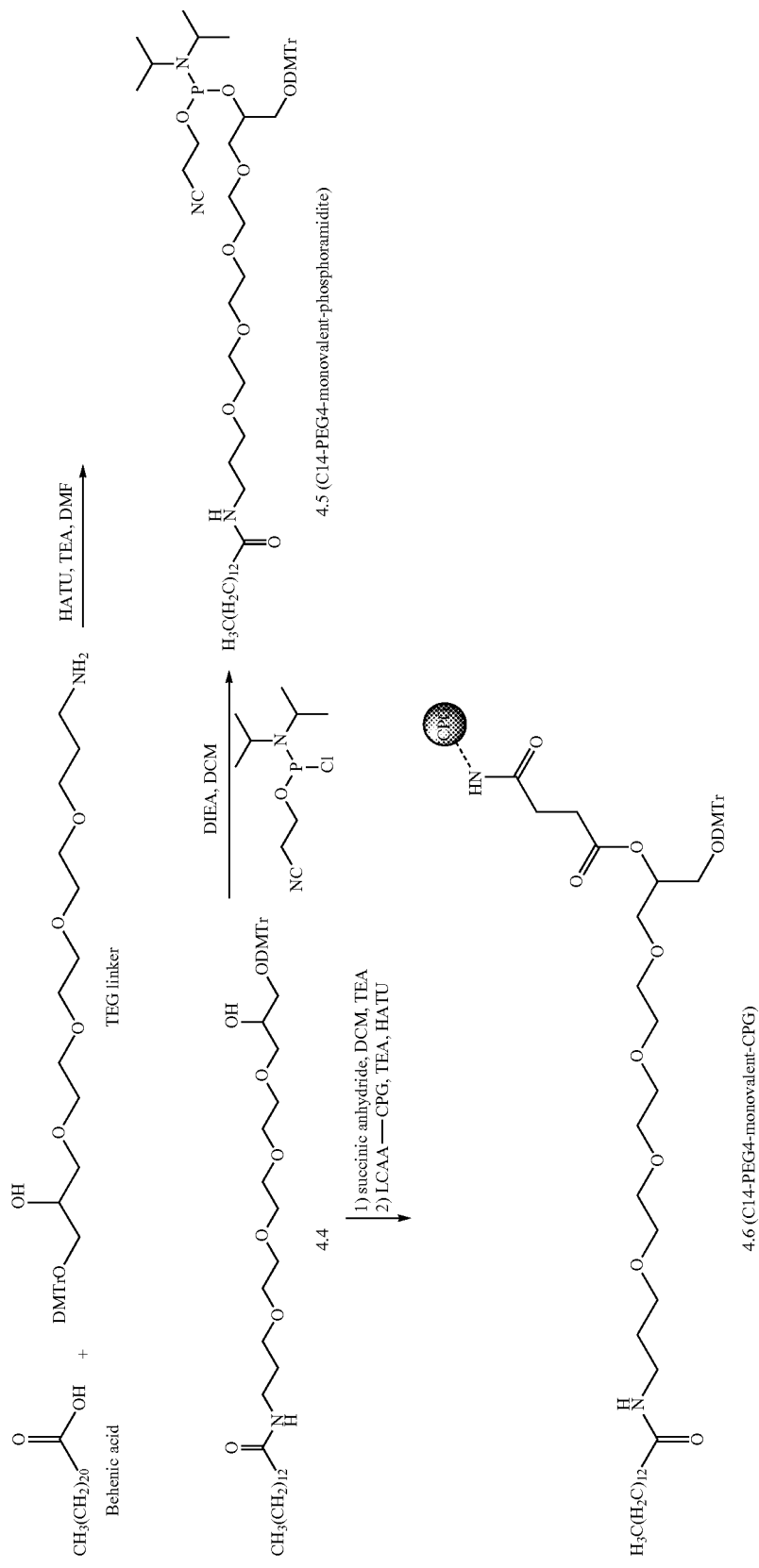

Compound 4.4: Myristic acid (0.5 g, 2.19 mmol) and TEG linker (1.38 g, 2.36 mmol) were dissolved in DMF (11 mL), and HATU (1.0 g, 2.63 mol) was added followed by DIEA (0.76 mL, 4.38 mmol). The reaction mixture was stirred at rt for 3 h, and TLC indicated reaction completion. The mixture was diluted with DCM (50 mL) and then poured into saturated NaHCO$_3$ solution (110 mL) with vigorous stifling. The organic phase was separated, and the aqueous phase was then extracted with DCM (50 mL×3). The combined organic phases were dried over Na$_2$SO$_4$, filtered, and concentrated to dryness. Crude compound 4.4 was purified by flash column chromatography eluted with 1% TEA in DCM: MeOH (0% to 10% MeOH) to obtain compound 4.4 (1.91 g, contain DMF). MS: found [M+AcOH−H]$^{31}$ =852.7; calc: [M+AcOH−H]−=852.5.

Compound 4.5 (C14-PEG4-monovalent-phosphoramidite): In a 250 mL RB flask compound 4.4 (1.42 g, 1.79 mmol) was dissolved in DCM (89.5 mL). 2-Cyanoethyl N,N-diisopropylchlorophosphoramidite (0.60 mL, 2.68 mmol) and DIEA (0.94 mL, 5.37 mmol) were added. The reaction mixture was stirred at rt for 2 h, and TLC confirmed reaction completion. This mixture was then poured into saturated NaHCO$_3$ (50 mL) and extracted with DCM (50 mL×2). The combined organic layer was dried over MgSO$_4$, filtered, and concentrated to dryness. The crude product was purified by flash column chromatography using 2% TEA in hexanes/EtOAc (0 to 85% EtOAc). The pure fractions were collected and concentrated to dryness to obtain compound 4.5 (0.57 g, 32%). MS: found: [M+NH4]$^+$=1012.1; calc: [M+NH4]$^+$=1012.2. $^{31}$ PNMR (mixture of diastereomers, CDCl$_3$): δ 149.726, 149.184.

Compound 4.6 (C14-PEG4-monovalent-CPG): Step 1: Compound 4.4 (0.50 g, 0.630 mmol) was dissolved in DCM (3.2 mL) and succinic anhydride (94.5 mg, 0.944 mmol) was then added followed by TEA (0.18 mL, 1.26 mmol). The reaction mixture was allowed to stir at rt overnight and TLC indicated reaction completion. Crude product was purified by flash column chromatography eluted with 1% TEA in DCM : MeOH (0% to 5% MeOH) to obtain the corresponding succinate as TEA salt (0.51 g, 80.9%). MS: found [M+NH4]$^+$=911.9; calc: [M+NH4]+=911.5.

Step 2: In a 250 mL RB flask succinate from step 1 (0.51 g, 0.512 mmol) was dissolved in MeCN (35 mL). HATU (0.208 g, 0.547 mmol) and DIEA (0.29 mL, 1.64 mmol) were added. After 5 min LCAA CPG (7.0 g, 500 Å) was added. The reaction mixture was rotated on a rotary evaporator at rt for 3 h. After filtration, this GPG was washed with MeCN (35 mL×3) and THF (35 mL×3) and dried under vacuum for 30 min. Loading was determined by standard DMTr assay by UV-Vis (498 nm) to be 58 µmol/g.

Capping: In a 250 mL RB flask THF (28 mL) was added to the uncapped CPG followed by pyridine (3.5 mL) and acetic anhydride (3.5 mL). The reaction was rotated on a rotary evaporator at rt for 15 min. The capped CPG was then filtered, washed with THF (35 mL), 10% pyridine in MeOH (35 ml×2), MeOH (35 mL), MeCN (35 mL×2), and DCM (35 mL). This capped CPG was dried under high vacuum for 30 min. Loading was determined by standard DMTr assay by UV-Vis (498 nm) to be 58 µmol/g. Ninhydrin test: negative.

Example 3. Synthetic Routes to Prepare Lipid-PEGylated Compounds of Formula (Ib)

General Synthetic Route to Prepare a Compound of Formula (Ib)

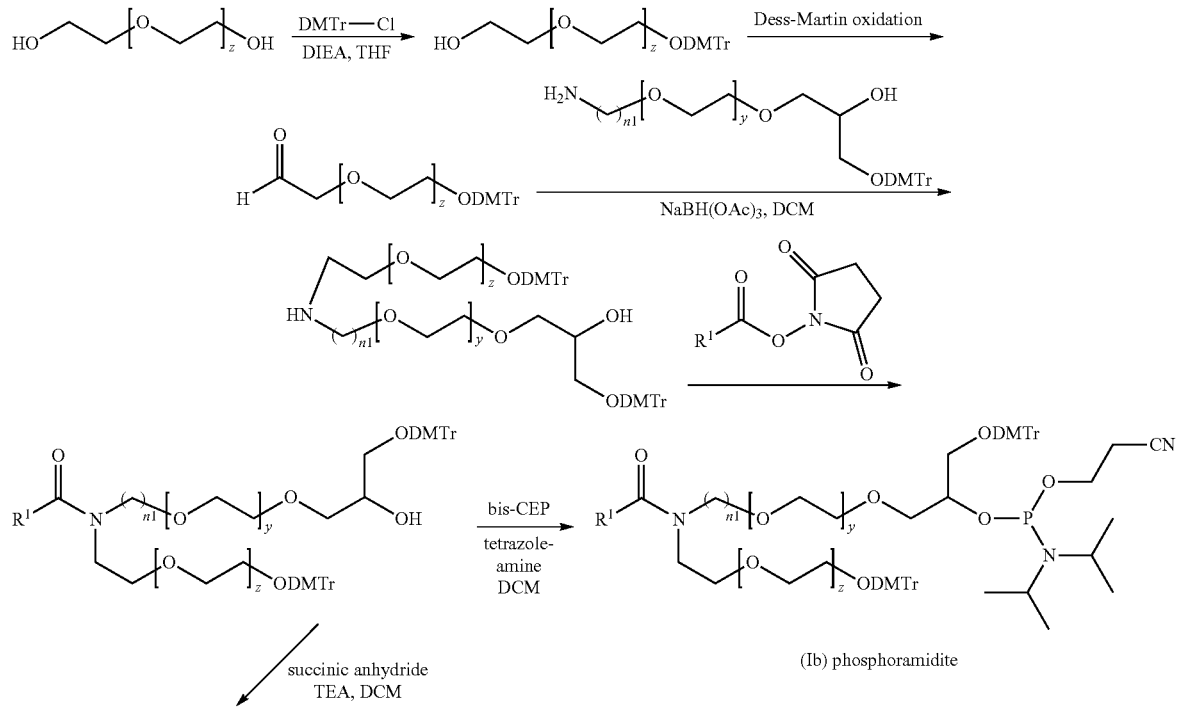

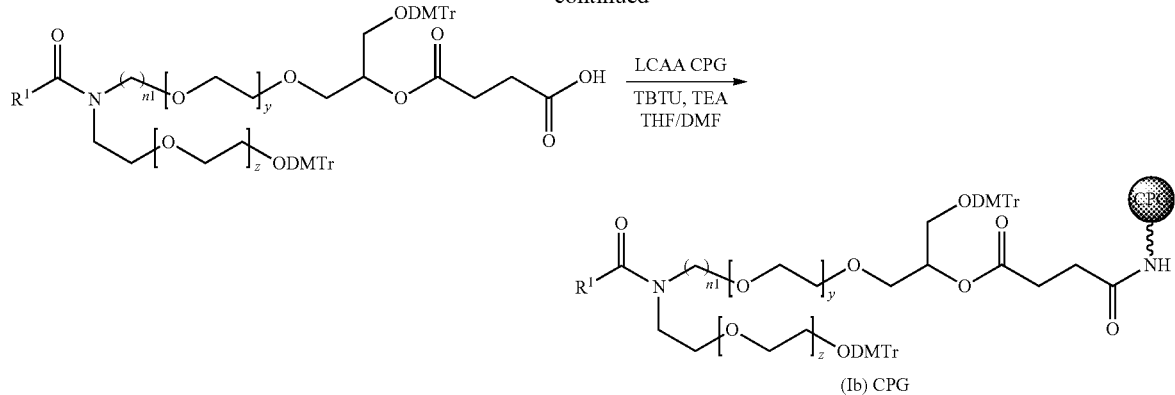

Scheme 5. Synthetic route to prepare C14-PEG-divalent-phosphoramidite 5.6 and C14-PEG-divalent-CPG 5.8 of Formula (Ib)

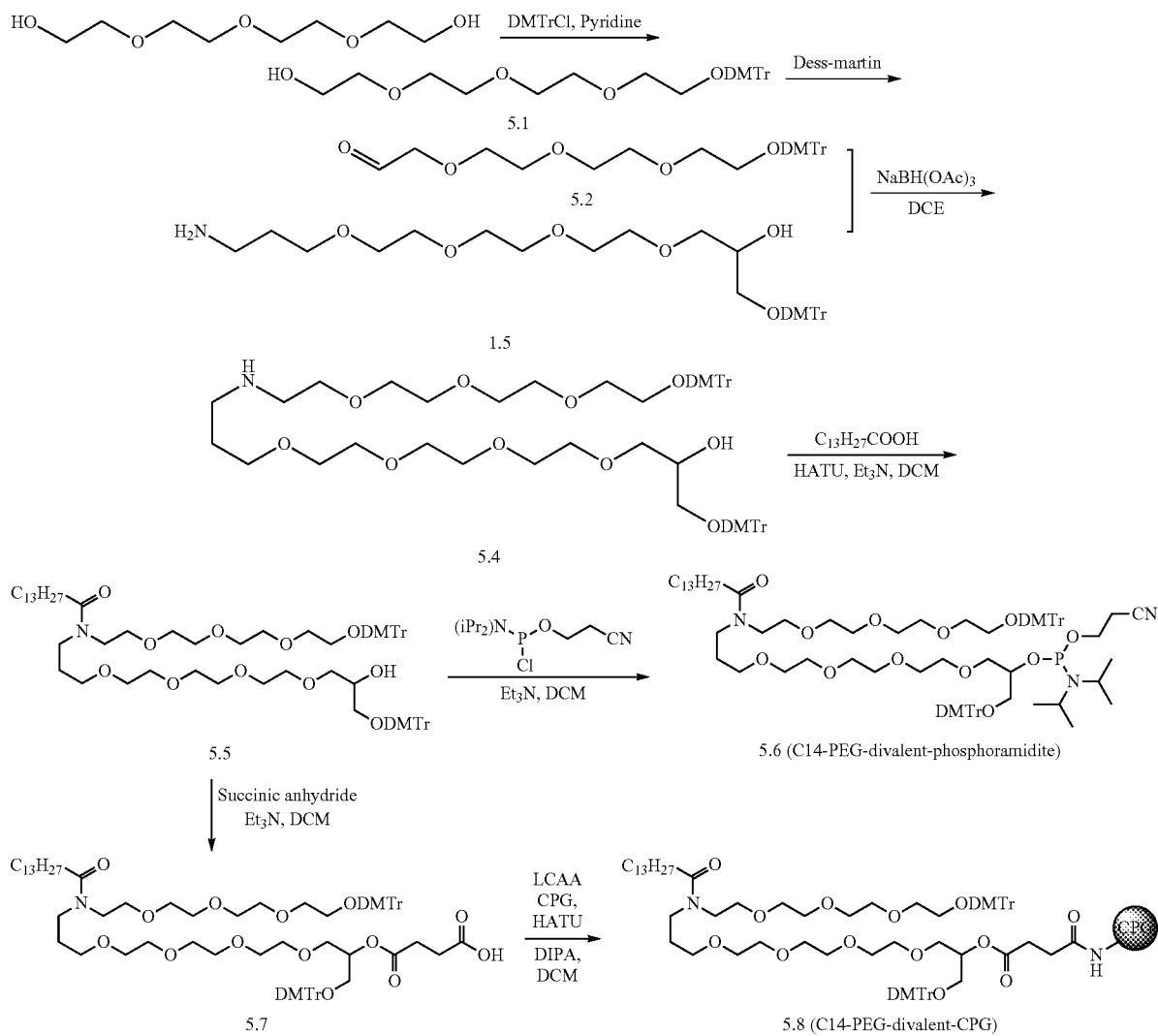

Compound 5.1: To a solution of tetraethylene glycol (14.3 g, 73.8 mmol) in pyridine (15 mL) was added DMTrCl (5.0 g, 14.8 mmol) in pyridine (20 mL), and the resulting reaction mixture was stirred at rt for 3 h. TLC indicated completion of the reaction. The solvent was removed in vacuo, and then the mixture was diluted with 25% aq. Na₂CO₃/ethyl acetate (50 mL/50 mL), the aqueous layer was then extracted with ethyl acetate (20 mL×2). The organic phase was washed with H$_2$O/brine (25 mL/25 mL), and the combined organic layers were dried over Na$_2$SO$_4$, filtered and concentrated. The residue was purified by column chromatography (eluting with 0-5% MeOH in DCM to give compound 5.1 (5.3 g, 72%) as a light-yellow oil. MS: found: [M+NH$_4$]$^+$=514.6; calc: [M+NH$_4$]$^+$=514.6.

Compound 5.2: To a solution of compound 5.1 (13.43 g, 27 mmol) in anhydrous DCM (150 mL) was added Dess-Martin periodinane (17.2 g, 40.5 mmol). The reaction mixture was stirred for 2 h at rt. TLC indicated completion of the reaction, and the mixture was diluted with aq. NaHCO$_3$/DCM (50 mL/50 mL). The aqueous layer was extracted with DCM (50 mL×2). The combined organic layers were dried over Na$_2$SO$_4$, filtered and concentrated. The residue was purified by column chromatography (eluting with 0-20% MeOH in DCM to give compound 5.2 (6.9 g, 52%) as a yellow oil. MS: found: [M+NH$_4$]$^+$=512.7; calc: [M+NH$_4$]$^+$=512.6.

Compound 5.4: To a solution of PEG linker 1.5 from Example 1(7.4 g, 12.7 mmol) and compound 5.2 (6.9 g, 14 mmol) in DCM (150 mL) was added NaBH(OAc)$_3$(3.8 g, 17.78 mmol). The reaction mixture was stirred for 3 h at rt. TLC indicated completion of the reaction, and the mixture was quenched by aq. NaHCO$_3$ (30 mL). The aqueous layer was extracted with DCM (50 mL×2). The combined organic layer was washed by brine (50 mL×2), dried over Na$_2$SO$_4$, filtered, and concentrate. The residue was purified by column chromatography (eluting with 0-10% MeOH in DCM to give compound 5.4 (5.53 g, 37%) as a light-yellow oil. MS: found: [M+H]$^+$=1062.9; calc: [M+H]$^+$=1063.3.

Compound 5.5: To a solution of compound 5.4 (3.97 g, 3.73 mmol) and myristic acid (1.0 g, 4.48 mmol) in anhydrous DCM (100 mL) was added Et$_3$N (1.6 mL, 11.2 mmol) and HATU (2.84 g, 7.46 mmol). The reaction mixture was stirred for 17 h at rt. TLC indicated completion of the reaction. The mixture was diluted with H$_2$O/DCM (50 mL/50 mL), and the aqueous layer was extracted with DCM (50 mL×2). The combined organic layer was washed by aq. NaHCO$_3$(50 mL ×2) and brine (50 mL×2), dried over Na$_2$SO$_4$, filtered and concentrated. The residue was purified by column chromatography (eluting with 0-5% MeOH in DCM to give compound 5.5 (2.44 g, 51%) as a light-yellow oil. MS: found: [M+NH$_4$]$^+$=1290.2; calc: [M+NH$_4$]$^+$=1290.7.

Compound 5.6 (C14-PEG-divalent-phosphoramidite): To a solution of compound 5.5 (1.9 g, 1.49 mmol) in anhydrous DCM (70 mL) was added Et$_3$N (452 mg, 4.47 mmol) and 2-cyanoethyl N,N-diisopropylchlorophosphoramidite (353 mg, 1.49 mmol). The reaction mixture was stirred for 15 h at rt. TLC indicated completion of the reaction. The mixture was diluted with aq. NaHCO$_3$/DCM (20 mL/20 mL), and the aqueous layer was extracted with DCM (20 mL×2). The combined organic layer was washed by aq. NaHCO$_3$ (20 mL×2), dried over Na$_2$SO$_4$, filtered, and concentrated. The residue was purified by column chromatography (eluting with 0-40% ethyl acetate in hexane-contained 1% Et$_3$N) to compound 5.6 (408 mg, 19%) as a light-yellow oil. MS: found: [M+NH$_4$]$^+$=1490.2; calc: [M+NH$_4$]$^+$=1490.9. $^{31}$PNMR (mixture of diastereomers, CDCl3): δ 149.6, 149.1.

Compound 5.7: To a solution of compound 5.5 (810 mg, 0.64 mmol) in DCM (32 mL) was added Et$_3$N (324 mg, 3.2 mmol) and succinic anhydride (165 mg, 1.65 mmol), and the mixture was stirred at rt for 48 h. TLC revealed completion of the reaction. The mixture was diluted with H$_2$O/DCM (20 mL/20 mL), and the aqueous layer was extracted with DCM (20 mL×2). The combined organic layer was washed with H$_2$O (20 mL×2) and brine (20 mL×2), dried over Na$_2$SO$_4$, filtered, and concentrated to give compound 5.7 (656 mg, 75%) as a yellow oil. MS: found: [M−H]$^-$=1371.0; calc: [M−H]$^-$=1371.7.

Compound 5.8 (C14-PEG-divalent-CPG): To a solution of compound 5.7 (618 mg, 0.45 mmol) in anhydrous acetonitrile (30 mL) was added HATU (171 mg, 0.45 mmol) and DIPEA (174 mg, 1.35 mmol). The mixture was stirred at rt for 10 min. Pretreated LCAA CPG 500A (6 g, loading: 75 µmol/g) was added. The resulting mixture was slowly agitated at 25° C. for 3 h. The mixture was then filtered, and this CPG was washed with acetonitrile (30 mL×3) and THF (30 mL×3) successively, and then it dried under reduced pressure for 3 h. Loading was determined by standard DMTr assay by UV-Vis (498 nm) to be 117 µmol/g.

Capping: To the CPG from above was added a mixture of Ac$_2$O (3 mL) and pyridine (3 mL) in anhydrous THF (24 mL). The resulting mixture was slowly agitated at 25° C. for 30 min. The mixture was filtered. The capped CPG was washed with THF (24 mL×3), 10% pyridine in MeOH (24 mL×3), MeOH (24 mL×3), acetonitrile (24 mL×2) and DCM (24 mL×1) successively. The capped CPG was dried under reduced pressure for 3 h (5.7 g). Loading was determined by standard DMTr assay by UV-Vis (498 nm) to be 125 µmol/g). Ninhydrin test: negative.

Example 4. Synthetic Routes to Prepare Lipid-PEGylated Compounds of Formula (Ic)

General Synthetic Route to Prepare a Compound of Formula (Ic)

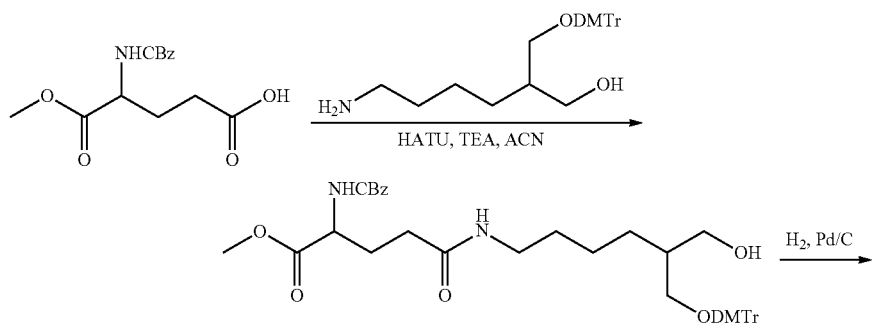

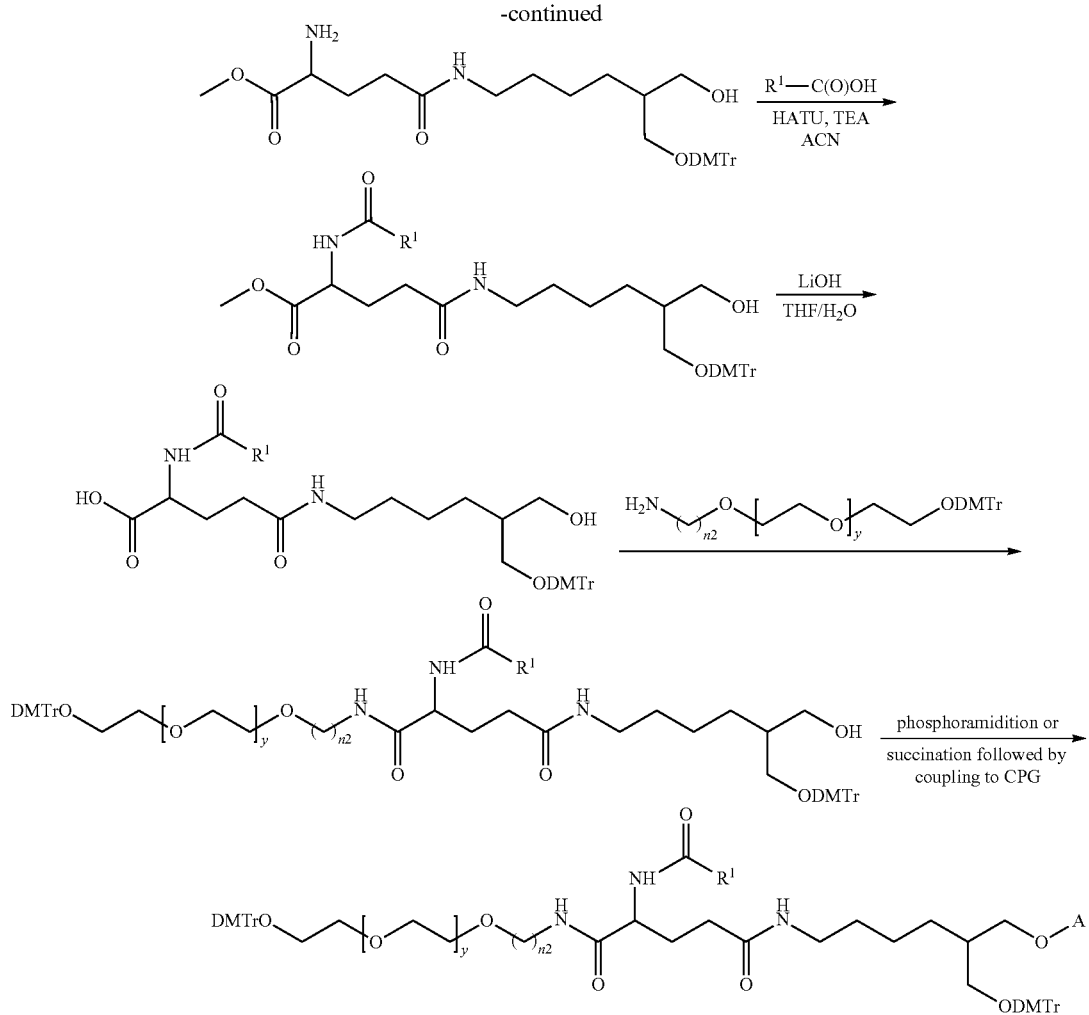
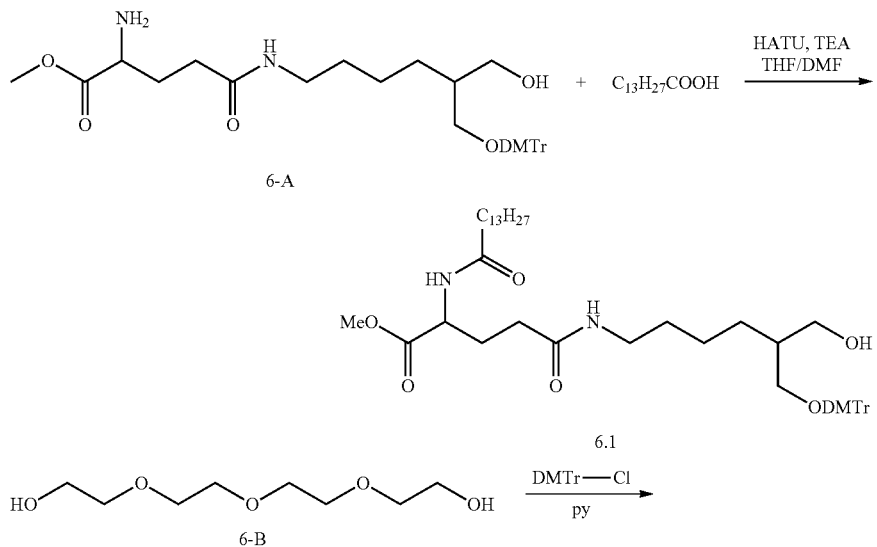
Scheme 6. Synthetic route to prepare C14-C7-divalent-CPG 6.5 of Formula (Ic)

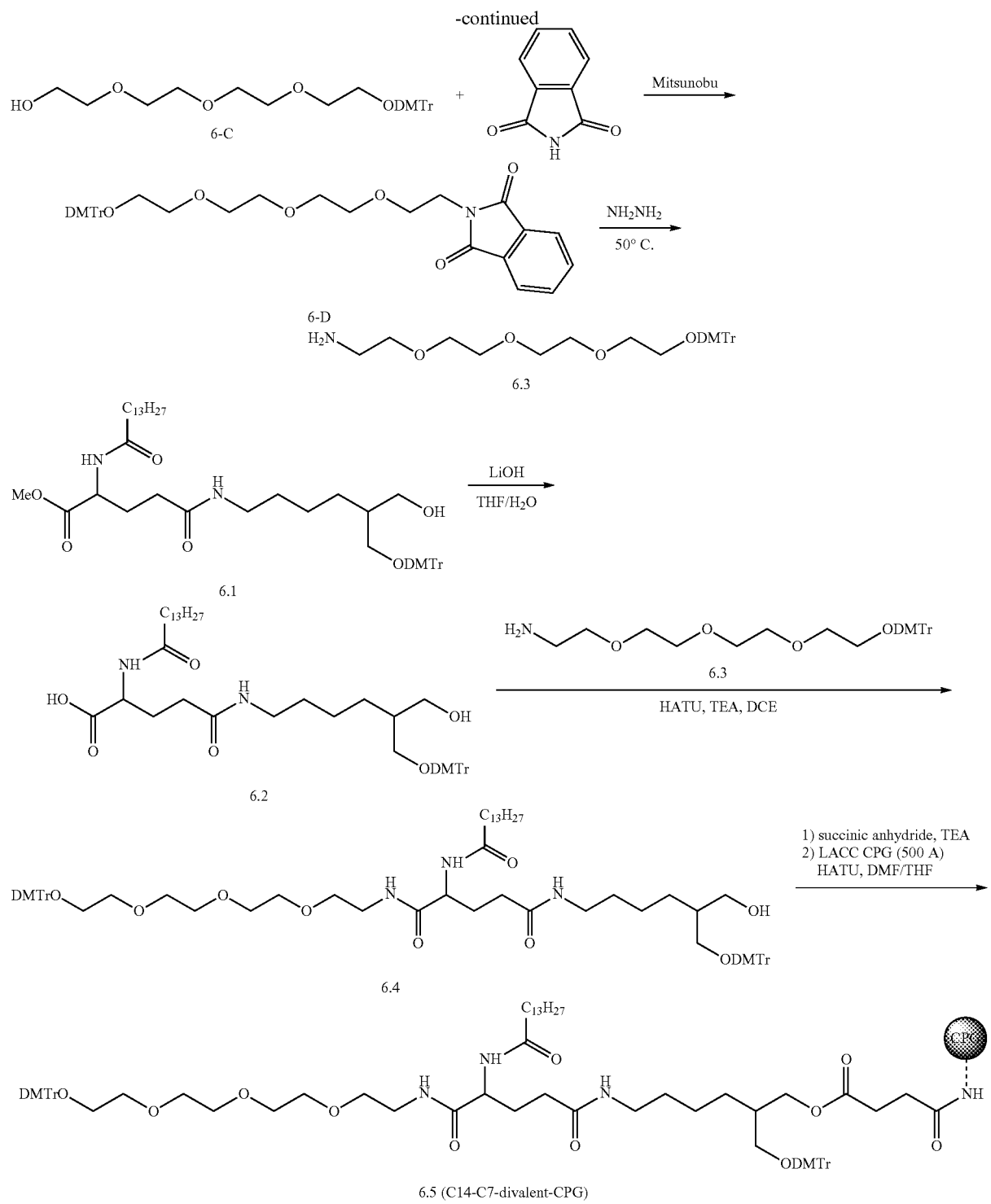

Compound 6.1: Compound 6-A (5.0 g, 8.43 mmol), Myristic acid (2.1 g, 9.27 mmol), HATU (4.16 g, 10.96 mmol) and TEA (2.35 mL, 16.86 mmol) were dissolved in DMF:THF=1:1 (50 mL) at rt. The reaction was monitored by TLC. Upon completion, the solvents were evaporated, and the residual was dissolved in DCM (50 mL). The solution was washed with water (3×50 mL) and brine (50 mL). The organic phase was dried over sodium sulfate, filtered, and concentrated. The residual was purified by FCC (eluted with DCM/TEA=100/0.5 to DCM/TEA/MeOH=100/0.5/10) to afford compound 6.1 (6.56 g, 97%). Rf=0.6 in (10% MeOH in DCM).

Compound 6.2: To a solution of compound 6.1 (6.56 g, 8.17 mmol) in THF (20 mL) was added a solution of LiOH (0.69 g, 16.3 mmol) in water (20 mL), and the resulting reaction mixture was stirred at rt overnight. TLC indicated reaction completion, and the solvent was removed in vacuo, and then the mixture was diluted with DCM (20 mL). White precipitates were formed, and the solid was filtered and washed with water (10 mL×2). The solid was dried under high vacuum overnight to obtain compound 6.2 as an off-white solid (3.46 g, 53.6%). MS: found: $[M-H]^-=787.8$; calc: $[M-H]^-=787.5$.

Compound 6-D: Step 1: Tetraethyleneglycol 6-B (57 g, 296 mmol) was dissolved in pyridine (500 mL), after which DMTrCl (10 g, 29.6 mmol) was added portion wise. The reaction was monitored by TLC. Upon completion the solvents were evaporated, and the residual was dissolved in DCM (500 mL) and washed with water (3×500 mL) and brine (500 mL). The organic phase was dried over sodium sulfate, filtered and concentrated to afford compound 6-C (17.5 g, with 3 g of pyridine) as a light-yellow oil. Rf=0.5 in (10% MeOH in DCM).

Step 2: Compound 6-C (16.5 g, 33.3 mmol), phthalimide (5.38 g, 36.6 mmol) and triphenylphosphine (10.5 g, 40 mmol) were dissolved in THF (150 mL). The mixture was cooled to 0° C. and DIAD (8.07 g, 40 mmol) was added portion wise. The reaction mixture was warmed up to rt and monitored by TLC. Upon completion the reaction was quenched by the addition of water (10 mL). THF was evaporated under vacuo, and the residual was redissolved in ethyl acetate (150 mL) and washed with water (3×150 mL) and brine (150 mL). The organic phase was dried over sodium sulfate, filtered and concentrated. The residual was purified by FCC (eluted with DCM/MeOH from 0% to 5% MeOH in DCM) to afford compound 6-D (18.3 g, 88%) as a yellow oil. Rf=0.3 in (5% MeOH in DCM).

Compound 6.3: Compound 6-D (18.3 g, 29.3 mmol) was dissolved in methanol (200 mL), after which hydrazine monohydrate (30 mL) was added. The reaction mixture was heated to 50° C. overnight and was monitored by TLC. Upon completion, the reaction mixture was cooled to rt and filtered. The liquid phase was concentrated and loaded to silica column (eluted with DCM to DCM/MeOH=70:30) to afford compound 6.3 (12 g, 83%) as a yellow oil. MS: found $[M+H]^+=496.4$; calc: $[M+H]^+=496.3$.

Compound 6.4: To a solution of compound 6.2 (3.46 g, 4.39 mmol) in anhydrous DCE (2.2 mL) and TEA (1.2 mL, 8.78 mmol) was added compound 6.3 (2.82 g, 5.70 mmol) and HATU (2.17 g, 5.70 mmol). The reaction mixture was stirred at rt for 5.5 h. TLC indicated reaction completion, and the mixture was quenched with water (50 mL). The organic layer was separated, and the aqueous layer was extracted with DCM (50 mL×2). The combined organic layers were dried over $Na_2SO_4$, filtered, and concentrated. The residue was purified by column chromatography (0-10% MeOH in 2% TEA/DCM) to obtain compound 6.4 as a white foam (1.7 g, 30.6%). MS: found: $[M+NH_4]^+=1284.2$; calc: $[M+NH_4]^+=1284.7$.

Compound 6.5 (C14-C7-divalent-CPG): Step 1: To a solution of compound 6.4 (0.91 g, 7.18 mmol) in DCM (3.6 mL) was added $Et_3N$ (0.20 mL, 1.44 mmol) and succinic anhydride (0.11 g, 1.08 mmol), and the mixture was stirred at rt for 20 h. TLC indicated reaction completion, and the mixture was concentrated to dryness. The residue was purified by column chromatography (0-12% MeOH in 2% TEA/DCM) to obtain a white solid (0.46 g, 46.9%). MS: found $[M-H]^-=1365.0$; calc: $[M-H]^-=1365.7$.

Step 2: Succinate TEA salt from step 1 (76, 0.45 mmol) was dissolved in anhydrous DMF/THF (2.5 mL/2.5 mL, 1/1 ratio), and DIPEA (27 μL, 0.156 mmol) was added. HATU (24 mg, 0.062 mmol) and pretreated LCAA-CPG (1 g, 500 Å, 40 μmol/g) were added to the mixture. The resulting mixture was slowly agitated at 25° C. for 3 h. The reaction mixture was then filtered, and this CPG was washed with acetonitrile (5 mL×2) and THF (5 mL×2) successively, and then dried under reduced pressure for 30 min.

Capping: To the CPG from above was added a mixture of $Ac_2O$ (0.5 mL) and pyridine (1.0 mL) in anhydrous THF (3.5 mL). The resulting mixture was slowly agitated at 25° C. for 15 min. The mixture was filtered, and the capped CPG was washed with THF (5 mL), 10% pyridine in MeOH (5 mL×2), MeOH (5 mL×2), acetonitrile (5 mL×2) and DCM (5 mL×2) successively. The capped CPG was dried under reduced pressure overnight (1.02 g). Loading was determined by standard DMTr assay by UV-Vis (498 nm) to be 62 μmol/g.

Scheme 7. Synthetic route to prepare C16-C7-divalent-CPG 7.9 and C16-C7-divalent-phosphoramidite 7.10 of Formula (Ic)

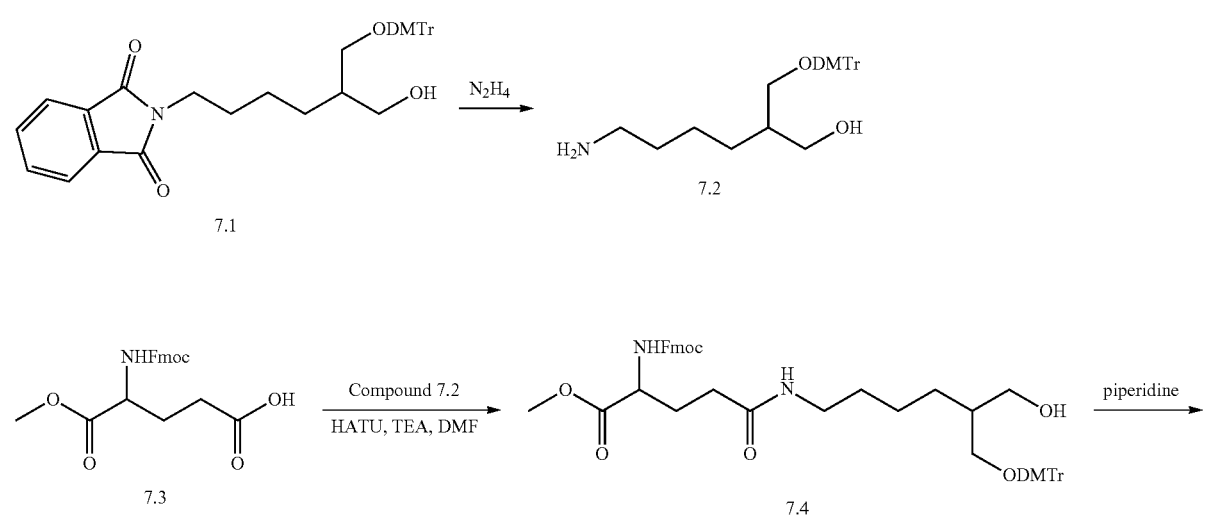

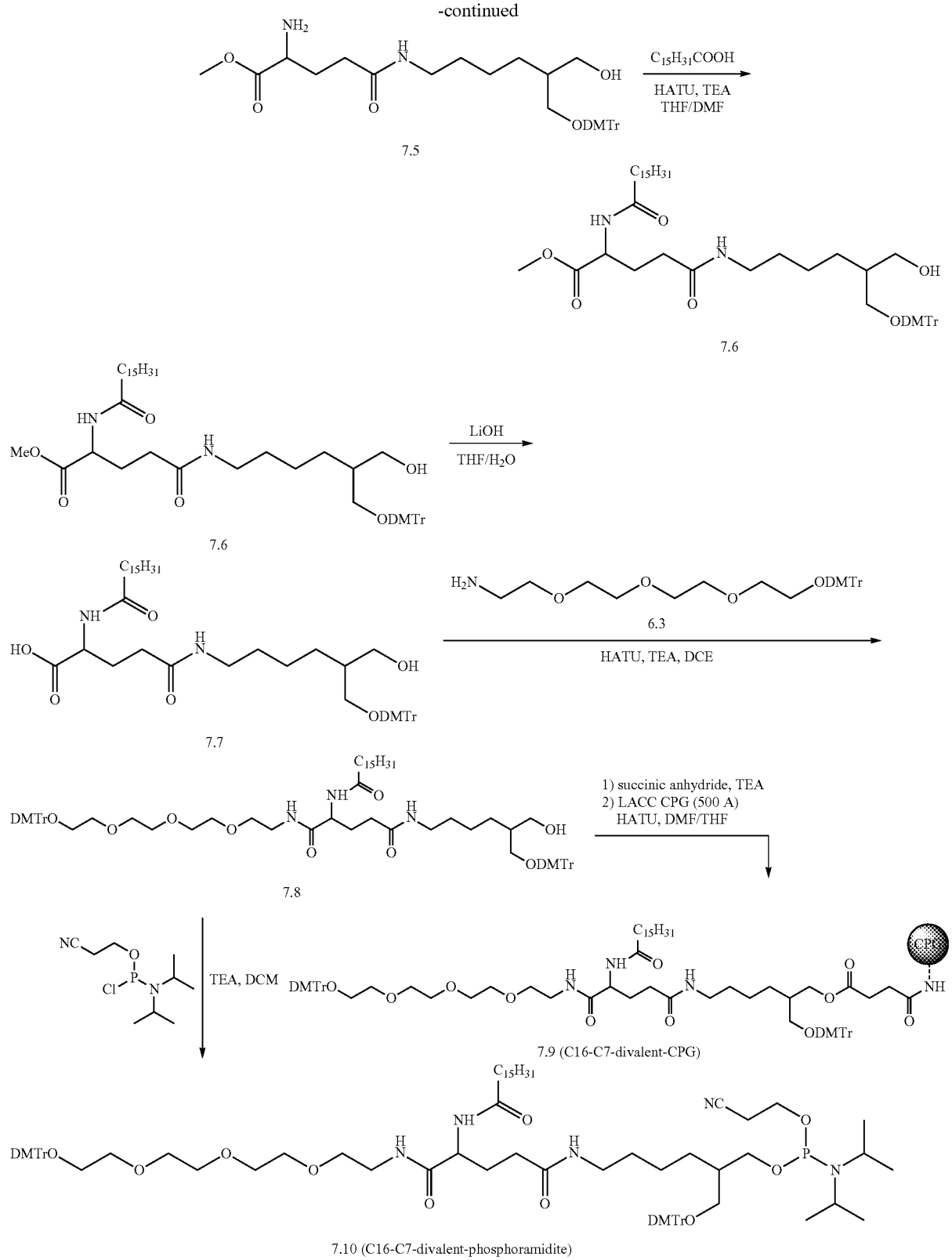

Compound 7.2: Compound 7.1 (41 g, 70.7 mmol) was dispersed in MeOH (400 mL), after which hydrazine monohydrate (41 mL) was added dropwise. The reaction mixture was heated to 50° C. overnight and was monitored by TLC. Upon completion the reaction mixture was cooled to rt and filtered. The liquid phase was concentrated and loaded to silica column (eluted with DCM/TEA=100: 0.5 to DCM/TEA/MeOH=100:0.5:20). Pure fractions were collected and concentrated to afford a crude material. This crude product was then recrystallized in a mixture of solvents (400 mL, DCM:ethyl acetate:heptanes=1:1:2), to afford compound 7.2 (30 g, 94%) as a white solid. MS: found: $[M+H]^+$=450.6; calc: $[M+H]^+$=450.3.

Compound 7.4: Compound 7.3 (21.3 g, 55.7 mmol), compound 7.2 (30 g, 66.8 mmol), HATU (27.5 g, 72.4 mmol) and TEA (11.6 ml, 83.6 mmol) were dissolved in 250 ml DMF. The reaction was allowed to react under rt and monitored by TLC and MS. Upon completion, the reaction mixture was diluted by 1L EA, washed by 3×1L saturate sodium bicarbonate, and 1L brine. The organic phase was dried over sodium sulfate, filtered and concentrated. The residual was purified by a glass column loaded with 330 g silica and eluted with DCM/TEA=100: 0.5 to DCM/TEA/MeOH=100:0.5:10, to afford 50 g crude compound 7.4 which was used directly for next step. MS: found: $[M+NH_4]^+$=832.8; calc: $[M+NH_4]^+$=832.4.

Compound 7.5: Compound 7.4 (50 g crude from previous step) was dissolved in DMF (300 mL), and piperidine (50 mL) was added dropwise at rt. The reaction mixture was monitored by TLC and LCMS. Upon completion the reaction mixture was diluted with EA (1 L), washed with saturate sodium bicarbonate (3×1 L), and brine (1 L). The organic phase was dried over sodium sulfate, filtered, and concentrated. The residual was purified by a silica column (eluted with DCM/TEA=100: 0.5 to DCM/TEA/MeOH=100:0.5:8) to afford compound 7.5 (23.3 g, 70% two steps). MS: found: $[M+H]^+$=593.4; calc: $[M+H]^+$=593.3.

Compound 7.6: Compound 7.5 (5.0 g, 8.43 mmol), palmitic acid (2.38 g, 9.27 mmol), HATU (4.16 g, 10.96 mmol) and TEA (2.35 mL, 16.86 mmol) were dissolved in DMF:THF (1:1, 50 mL) at rt. The reaction mixture was monitored by TLC. Upon completion the solvents were evaporated, and the residual was dissolved in DCM (50 mL). The solution was washed with water (3×50 mL) and brine (50 mL). The organic phase was dried over sodium sulfate, filtered and concentrated. The residual was purified by FCC (eluted with DCM/TEA=100:0.5 to DCM/TEA/MeOH=100:0.5:10) to afford compound 7.6 (3.4 g, 48.6%). Rf=0.6 in (10% MeOH in DCM).

Compound 7.7: Compound 7.6 (1.4 g, 1.7 mmol) and lithium hydroxide monohydrate (150 mg, 3.4 mmol) were dissolved in THF:water (1:1, 20 mL). The reaction mixture was allowed to stir at rt overnight and was monitored by TLC. Upon completion THF was evaporated, and the residual was diluted to water(100 mL) and washed with DCM (5×100 mL). The organic phase was dried over sodium sulfate, filtered and concentrated to afford compound 7.7. MS found: $[M-H]^-$=815.9; calc: $[M-H]^-$=815.5.

Compound 7.8: To a solution of compound 7.7 (1.4 g, 1.70 mmol) in DCE (8.5 mL) and TEA (1.2 mL, 8.78 mmol) was added PEG linker 6.3 (1.01 g, 2.04 mmol) and HATU (2.17 g, 5.70 mmol). The reaction mixture was stirred at rt for 4.5 h. TLC indicated reaction completion, and the mixture was quenched with 5% NaHCO3 in water (20 mL), and the reaction mixture was diluted with DCM (10 mL). The organic layer was separated, and the aqueous layer was extracted with ethyl acetate (10 mL×2). The combined organic layers were dried over $Na_2SO_4$, filtered, and concentrated. The residue was purified by column chromatography (0-10% MeOH in 2% TEA/DCM) to obtain compound 7.8 as a white foam (1.7 g, 30.6%). MS: found: $[M+NH_4]^+$=1312.0; calc: $[M+NH_4]^+$=1312.7.

Compound 7.9 (C16-C7-divalent-CPG): Step 1: To a solution of compound 7.8 (385 mg, 0.298 mmol) in DCM (15 mL) was added $Et_3N$ (151 mg, 1.49 mmol) and succinic anhydride (77.4 mg, 0.774 mmol), and the mixture was stirred at rt for 24 h. TLC revealed completion of the reaction. The mixture was diluted with $H_2O$/DCM (15 mL/15 mL), and the aqueous layer was extracted with DCM (10 mL×2). The combined organic layer was washed with $H_2O$ (10 mL×2) and brine (10 mL×2), dried over $Na_2SO_4$, filtered, and concentrated. The residue was purified by column chromatography (eluting with 0-5% MeOH in DCM to give the corresponding succinate (211 mg, 50%) as a yellow oil. MS: found: $[M-H]^-$=1393.8; calc: $[M-H]^-$=1393.2.

Step 2: To a solution of succinate from above (190 mg, 0.1365 mmol) in anhydrous acetonitrile (9.1 mL) was added HATU (52 mg, 0.1365 mmol) and DIPEA (53 mg, 0.1365 mmol). The mixture was stirred at rt for 10 min. Pretreated LCAA CPG 500A (1.82 g, loading: 75 μmol/g) was added. The resulting mixture was slowly agitated at 25° C. for 3 h. The mixture was then filtered, and this CPG was washed with acetonitrile (9.1 mL×3) and THF (9.1 mL×3) successively, and then dried under reduced pressure for 3 h. Loading was determined by standard DMTr assay by UV-Vis (498 nm) to be 106 μmol/g.

Capping: To the CPG from step 2 was added a mixture of $Ac_2O$ (0.91 mL) and pyridine (0.91 mL) in anhydrous THF (7.28 mL). The resulting mixture was slowly agitated at 25° C. for 30 min. The mixture was filtered, and the capped CPG was washed with THF (9.1 mL×3), 10% pyridine in MeOH (9.1 mL×3), MeOH (9.1 mL×3), acetonitrile (9.1 mL×2) and DCM (9.1 mL×1) successively. The capped CPG was dried under reduced pressure for 3 h (1.68 g). Loading was determined by standard DMTr assay by UV-Vis (498 nm) to be 104 μmol/g). Ninhydrin test: negative.

Compound 7.10: To a solution of compound 7.8 (388 mg, 0.3 mmol) in anhydrous DCM (15 mL) was added $Et_3N$ (91 mg, 0.9 mmol) and 2-cyanoethyl N,N-diisopropylchlorophosphoramidite (71 mg, 0.3 mmol). The reaction mixture was stirred for 20 h at rt. TLC indicated completion of the reaction. The mixture was diluted with aq. $NaHCO_3$/DCM (10 mL/10 mL), and the aqueous layer was extracted with DCM (10 mL×2). The combined organic layer was washed with aq. $NaHCO_3$(10 mL×2), dried over $Na_2SO_4$, filtered, and concentrated. The residue was purified by column chromatography (eluting with 0-60% ethyl acetate in hexane-contained 1% $Et_3N$) to obtain compound 7.10 (155 mg, 34%) as a light-yellow oil. MS: found: $[M+NH_4]^+$=1512.9; calc: $[M+NH_4]^+$=1512.3. $^{31}P$ NMR (mixture of diastereomers, $CDCl_3$, d.r.=1.06:1): δ 147.3, 147.1

Example 5. Preparation of Lipid-PEGylated Compound-conjugated Oligonucleotides

To demonstrate the usage of mono/di-valent lipid-PEG phosphoramidites in oligonucleotide synthesis, an oligonucleotide sequence (5'-TTTTTTTTTT-3'; SEQ ID. No. 1), coupled with a mono lipid-PEG phosphoramidite "X" was prepared to form 5'-X-TTTTTTTTT-3' as shown in FIG. 1. In addition, an oligonucleotide sequence (5'-TTTTT-3') was first coupled with a divalent lipid-PEG phosphoramidite "X" to form XTTTTT and subsequently continued to add additional five T to each of the available hydroxy terminals of the divalent lipid-PEG phosphoramidite X to form $(TTTTT)_2$-X-TTTTT. In FIG. 1, "X" represents either a monovalent (circle) or divalent (triangle) lipid-PEG phosphoramidite compound X1 through X4. The following compounds were generated are labeled as X1T10 through X3T10 and $(T5)_2X4T5$.

The oligonucleotides X1T10 through X3T10 and (T5)₂X4T5 were synthesized using the solid-phase phosphoramidite method. A DMT-dT solid support was packed in an empty column and put into the MerMade 6 synthesizer. The synthetic scale was 0.2 1.μmol. The oligonucleotide synthesis cycle included the following steps:

(1) detritylation with 3% trichloroacetic acid in dichloromethane for 45 second two times, followed by acetonitrile washing.

(2) coupling with 0.1 M DMT-dT-CE-Phosphoramidite (5'-O-(4,4'-Dimethoxytrityl)-thymidine-3'-cyanoethyl Phosphoramidite) in acetonitrile and 0.5 M activator (tetrazole in acetonitrile) for 1 minute two times, followed by acetonitrile washing. After coupling a divalent phosphoramidite, the time was increased to optimize the coupling efficiency.

(3) oxidation with iodine (0.015 M iodine in water/pyridine/THF 2/20/78) for 45 second, followed by acetonitrile washing.

(4) capping with a mixture of acetic anhydride, pyridine, and THF for 45 second, followed by acetonitrile washing.

Steps (1) through (4) were repeated 4 or 9 times for synthesizing the full elongated sequences from the dT solid support. At the position to couple mono/di-valent lipid-PEG phosphoramidites, the sample detritylation, coupling, oxidation, and capping steps were performed, while the coupling was performed using a mixture of 0.05-0.15 M mono/di-valent lipid-PEG phosphoramidites in acetonitrile and 0.5 M activator for 3 minutes for two times, followed by acetonitrile washing.

After synthesis, the oligonucleotide-bounded solid supports were treated with a 1:1 mixture of aqueous ammonium hydroxide and methylamine at 55° C. for 2 hr for cleavage and deprotection. Upon completion, the liquid phase was collected and heat dried in vacuum. The dried residue was dissolved in water and analyzed by reverse-phase HPLC (Agilent 1260) and LC-MS (Applied Biosystems 4000 Q-Trap). The HPLC gradient was 10-90% D in 20 min, with A: 50 mM triethylammonium acetate in water and D: acetonitrile. The retention time (RT), MS calculated, MS found, and full-length product purity (FLP) for each sequence are shown in Table 1.

Figure 2:
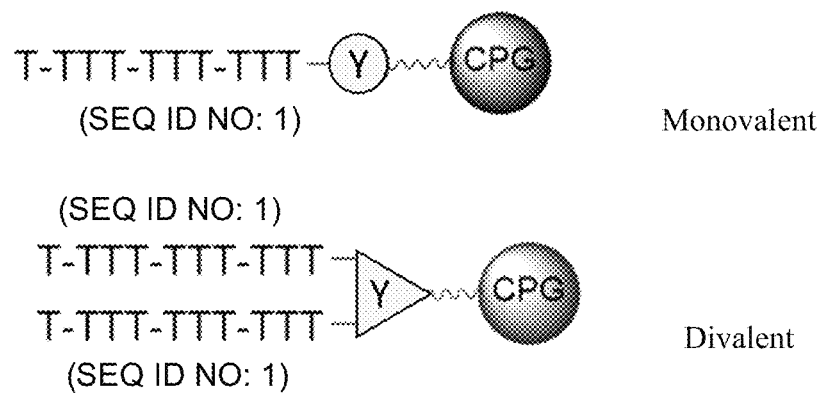
FIG. 2 depicts an oligonucleotide sequence coupled with monovalent and divalent lipid-PEG solid supports according to certain embodiments of the present disclosure.

Example 6. Preparation of Lipid-PEGylated Compound-Conjugated Oligonucleotides on Solid Supports To demonstrate the usage of mono/di-valent lipid-PEG CPG solid supports in oligonucleotide synthesis, an oligonucleotide sequence (5'-TTTTTTTTTT-3'; SEQ ID. No. 1), coupled with a mono/divalent lipid-PEG support "Y" was prepared to form 5'-TTTTTTTTTT-Y-3' as shown in FIG. 2. In FIG. 2, "Y" represents either a monovalent (circle) or divalent (triangle) lipid-PEG CPG compound Y1 through Y6. The following solid support bound compounds were generated are labeled as T10Y1 through T10Y3 and (T10)₂Y4 through (T10)₂Y6.

The oligonucleotides T10Y1 through T10Y3 and (T10)₂Y4 through (T10)₂Y6 were synthesized using the solid-phase phosphoramidite method. A mono/di-valent lipid-PEG solid supports (Y) was packed in an empty column and put into the MerMade 6 synthesizer. The synthetic scale was 0.5-2 1.μmol. The oligonucleotide synthesis cycle included the following steps:

(1) detritylation with 3% trichloroacetic acid in dichloromethane for 45 second two times, followed by acetonitrile washing;

(2) coupling with 0.1 M DMT-dT-CE-Phosphoramidite (5'-O-(4, 4'-Dimethoxytrityl)-thymidine-3'-cyanoethyl Phosphoramidite) in acetonitrile and 0.5 M activator (tetrazole in acetonitrile) for 1 minute two times, followed by acetonitrile washing. For divalent CPG, the time was increased to optimize the coupling efficiency;

(3) oxidation with iodine (0.015 M iodine in water/pyridine/THF 2/20/78) for 45 second, followed by acetonitrile washing;

(4) capping with a mixture of acetic anhydride, pyridine, and THF for 45 second, followed by acetonitrile washing.

Steps (1) through (4) were repeated 10 times for synthesizing T10 elongated from the mono/di-valent lipid-PEG solid supports and finished by the final detritylation with acetonitrile washing.

After synthesis, the oligonucleotide-bounded solid supports were treated with a 1:1 mixture of aqueous ammonium hydroxide and methylamine at 55° C. for 2 hr for cleavage and deprotection. Upon completion, the liquid phase was collected and heat dried in vacuum. The dried residue was dissolved in water and analyzed by reverse-phase HPLC (Agilent 1260) and LC-MS (Applied Biosystems 4000 Q-Trap). The HPLC gradient was 10-90% D in 20 min, with A: 50 mM triethylammonium acetate in water and D: acetonitrile. The retention time (RT), MS calculated, MS found, and full-length product purity (FLP) for each sequence are shown in Table 2.

TABLE 1

Usage tests of mono/di-valent lipid-PEG phosphoramidite

| X | Phosphoramidite | Amidite Purity (%) | Oligo# | Retention Time (min) | FLP (%) | Mass Calculated | Mass Found |
|---|---|---|---|---|---|---|---|
| Compound 2.8 | C14-PEG3-monovalent | N/A | X1T10 | 16.685 | 16.7 | 3475.59 | 3476.43 |
| Compound 4.5 | C14-PEG4-monovalent | 96% | X2T10 | 13.940 | 62.4 | 3533.67 | 3535.25 |
| Compound 3.3 | C22-PEG4-monovalent | 95.7% | X3T10 | 18.133 | 54.2 | 3645.89 | 3648.61 |
| Compound 5.6 | C14-PEG-divalent | 98.6% | (T5)₂X4T5 | 11.673 | 52.0 | 5230.82 | 5232.78 |

TABLE 2

Usage tests of mono/di-valent lipid-PEG CPGs

| Y | CPG | Loading (μmol/g) | Oligo# | Retention Time (min) | FLP (%) | Mass Calculated | Mass Found |
|---|---|---|---|---|---|---|---|
| Compound 2.9 | C14-PEG3-monovalent | 48 | T10Y1 | 16.258 | 87.9 | 3475.59 | 3476.76 |
| Compound 4.6 | C14-PEG4-monovalent | 58 | T10Y2 | 13.989 | 98.3 | 3533.67 | 3535.37 |
| Compound 3.2 | C22-PEG4-monovalent | 49 | T10Y3 | 18.183 | 94.1 | 3645.89 | 3647.48 |
| Compound 5.8 | C14-PEG-divalent | 117 | (T10)$_2$Y4 | 12.110 | 68.3 | 6753.85 | 6756.00 |
| Compound 6.5 | C14-C7-divalent | 62 | (T10)$_2$Y5 | 11.908 | 76.2 | 6747.85 | 6748.68 |
| Compound 7.9 | C16-C7-divalent | 105 | (T10)$_2$Y6 | 12.487 | 54.1 | 6771.87 | 6777.54 |

What is claimed is:

1. A compound of Formula (I):

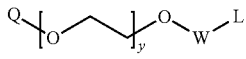

(I)

Wherein Q is

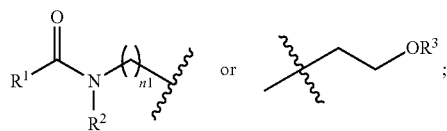

W is $C_{1-10}$ alkylene, 2 to 10 membered heteroalkylene, or

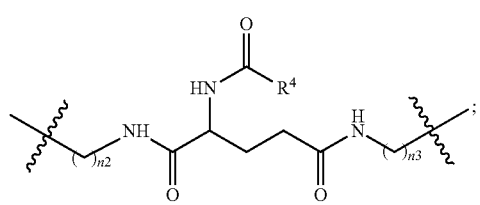

L is

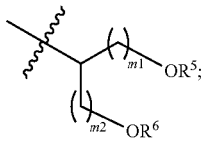

each of $R^1$ and $R^4$ is independently $C_{1-22}$ alkyl or $C_{2-22}$ alkenyl;

$R^2$ is

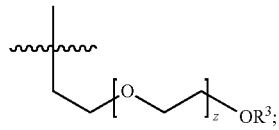

each of $R^3$ and $R^5$ is independently H or a hydroxyl protecting group;

$R^6$ is hydrogen, a phosphoramidite moiety, —C(=O)CH$_2$CH$_2$C(=O)R$^{6A}$, or —P(OR$^{6B}$)NR$^{6C}$R$^{6D}$;

$R^{6A}$ is —OH, —OR$^7$ or —NR$^8$R$^9$;

each of $R^{6B}$, $R^{6C}$ and $R^{6D}$ is independently H, $C_{1-6}$ haloalkyl, or optionally substituted $C_{1-6}$ alkyl;

$R^7$ is optionally substituted $C_{1-6}$ alkyl or a hydroxy protecting group; and each of $R^8$ and $R^9$ is independently H, optionally substituted $C_{1-6}$ alkyl or an amino protecting group;

each of y and z is independently an integer of 1 to 100;

each of n1, n2 and n3 is independently an integer of 1 to 10; and each of m1 and m2 is independently 0, 1, 2 or 3;

provided that when Q is

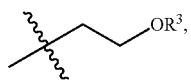

then W is

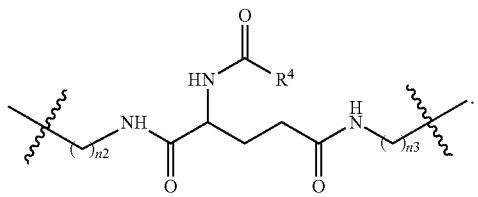

2. The compound of claim 1, wherein Q is

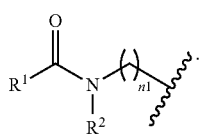

3. The compound of claim 2, wherein $R^1$ is $C_{5-22}$ alkyl.
4. The compound of claim 2, wherein $R^1$ is $C_{5-22}$ alkenyl.
5. The compound of claim 4, wherein $R^1$ is

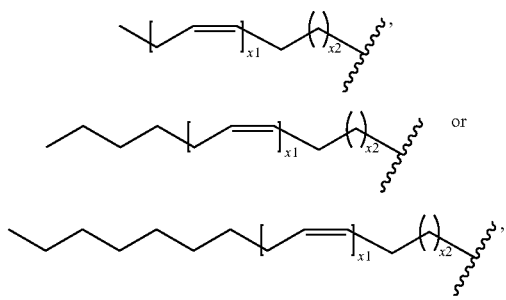

wherein each of x1 and x2 is independently an integer of 1 to 6.

6. The compound of claim 2, wherein z is an integer of 1, 2, 3, 4, 5, 6, 7, 8, 9 or 10.
7. The compound of claim 2, wherein n1 is 2 or 3.
8. The compound of claim 1, wherein W is —$CH_2$—.
9. The compound of claim 1, wherein Q is

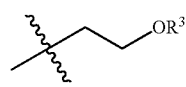

and W is

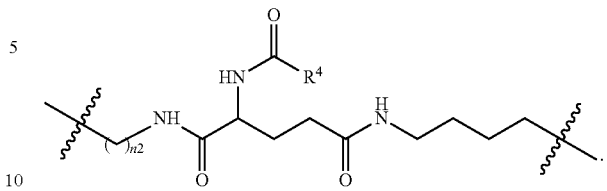

10. The compound of claim 9, wherein $R^4$ is $C_{5-22}$ alkyl.
11. The compound of claim 9, wherein $R^4$ is $C_{5-22}$ alkenyl.
12. The compound of claim 11, wherein $R^4$ is

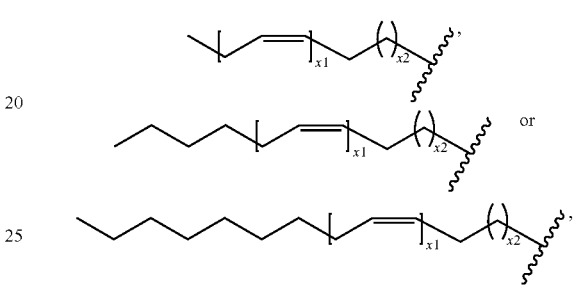

wherein each of x1 and x2 is independently an integer of 1 to 6.

13. The compound of claim 9, wherein n2 is 2 or 3.
14. The compound of claim 1, wherein $R^3$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl and 9-(4-methoxyphenyl)xanthen-9-yl.
15. The compound of claim 1, wherein L is

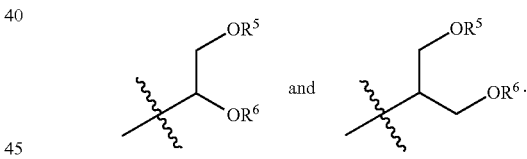

16. The compound of claim 15, wherein $R^5$ is a trityl type of hydroxy protecting group selected from the group consisting of (4-methoxyphenyl)diphenylmethyl, bis(4-methoxyphenyl)phenylmethyl, tris(4-methoxyphenyl)methyl, 9-phenylxanthen-9-yl and 9-(4-methoxyphenyl)xanthen-9-yl.
17. The compound of claim 15, wherein $R^6$ is —C(=O)$CH_2CH_2$C(=O)OH.
18. The compound of claim 15, wherein $R^6$ is

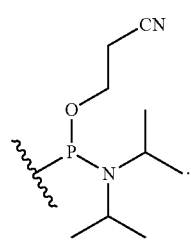 [SMILES: *P(OCCC#N)N(C(C)C)C(C)C]

19. The compound of claim 1, wherein y is 2, 3, 4, 5, 6 or 7.
20. The compound of claim 1, wherein $R^5$ is bis(4-methoxyphenyl)phenylmethyl.
21. The compound of claim 1, selected from the group consisting of:
22. A solid support comprising a compound of Formula (I) covalently attached thereto,
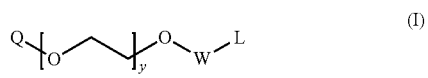
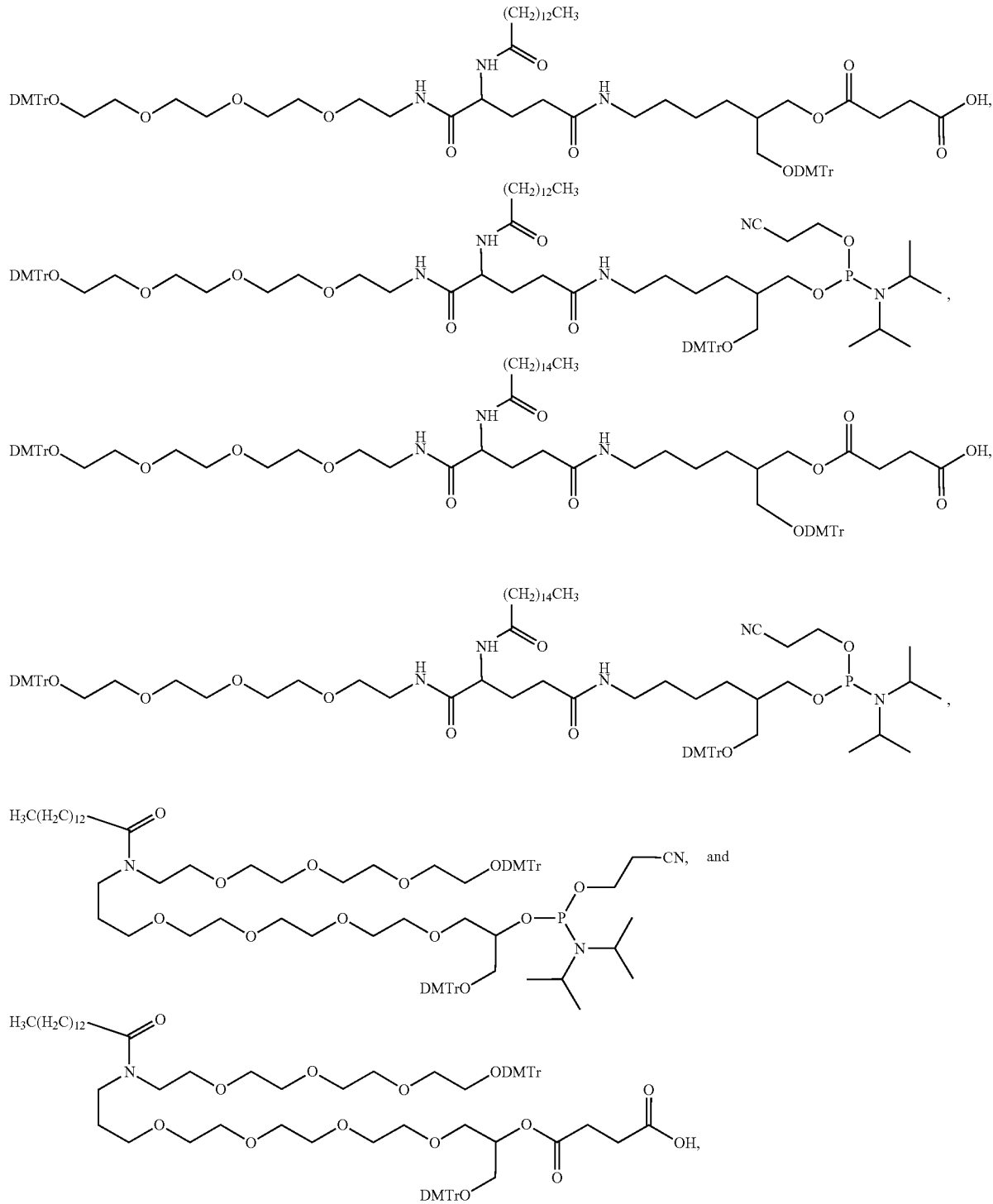
and pharmaceutically acceptable salts thereof.

wherein Q is

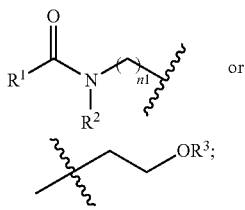 or

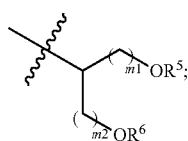

W is $C_{1-10}$ alkylene, 2 to 10 membered heteroalkylene, or

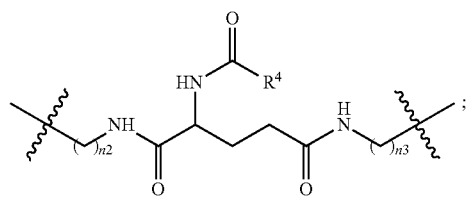

L is

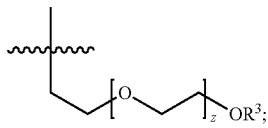

each of $R^1$ and $R^4$ is independently $C_{1-22}$ alkyl or $C_{2-22}$ alkenyl;

$R^2$ is

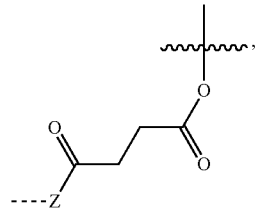

each of $R^3$ and $R^5$ is independently H or a hydroxyl protecting group;
$R^6$ is —C(=O)CH$_2$CH$_2$C(=O)R$^{6A}$;
$R^{6A}$ is —OH, —OR$^7$ or —NHR$^8$;
$R^7$ is optionally substituted $C_{1-6}$ alkyl or a hydroxy protecting group; and
$R^8$ is H, optionally substituted $C_{1-6}$ alkyl or an amino protecting group;
each of y and z is independently an integer of 1 to 100;

each of n1, n2 and n3 is independently an integer of 1 to 10; and
each of m1 and m2 is independently 0, 1, 2 or 3;
provided that when Q is

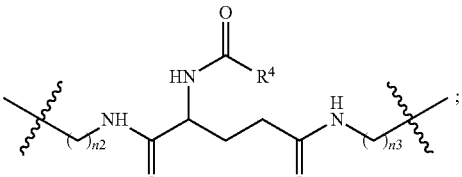

then W is

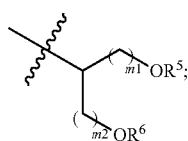

wherein the compound is covalently attached to the solid support via a moiety of $R^6$;

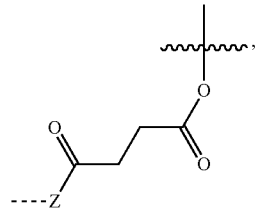

wherein Z is O or NH, and wherein the dashed line refers to the connection with the solid support, optionally through an additional linker, and wherein the squiggly line refers to the point of the attachment of the oxygen atom that is covalently attached to $R^6$ of the compound, to the remaining portion of the compound.

23. The solid support of claim 22, wherein $R^5$ is bis(4-methoxyphenyl)phenylmethyl.

24. The solid support of claim 22, wherein the compound is incorporated into a nucleoside analog or an oligonucleotide sequence.

25. A method of preparing a synthetic oligonucleotide or polynucleotide, comprising reacting a compound of claim 1, with one or more nucleoside analogs, an oligonucleotide, or polynucleotide.

26. The method of claim 25, wherein the oligonucleotide or polynucleotide comprises siRNA.

27. The method of claim 25, wherein the reaction is conducted on a solid support.

* * * * *

UNITED STATES PATENT AND TRADEMARK OFFICE
CERTIFICATE OF CORRECTION

| | | |
|---|---|---|
| PATENT NO. | : 12,098,371 B2 | Page 1 of 3 |
| APPLICATION NO. | : 18/451013 | |
| DATED | : September 24, 2024 | |
| INVENTOR(S) | : Mufa Zou et al. | |

It is certified that error appears in the above-identified patent and that said Letters Patent is hereby corrected as shown below:

In the Specification

Column 3, Line 36, delete "—C(=0)" and insert -- —C(=O) --.

Column 3, Line 48 (approx.), delete "and p each of" and insert -- and each of --.

Column 9, Lines 61-62, delete "thiamorpholine, thiamorpholine sulfoxide, thiamorpholine sulfone" and insert -- thiomorpholine, thiomorpholine sulfoxide, thiomorpholine sulfone --.

Column 21, Line 66, delete "xis 2, 3, 4, 5, or 6" and insert -- x1 is 2, 3, 4, 5, or 6 --.

Column 30, Line 57 (approx.), delete "LiAlH$_4$" and insert -- LiAlH$_4$ --.

Column 31, Line 32, delete "DMTrC1" and insert -- DMTrCl --.

Column 31-32, Line 59 (approx.), delete "(Ia)-phosporamidite" and insert -- (Ia)-phosphoramidite. --.

Column 33-34, Lines 32-33 (approx.), delete "2-Cyanoethyl N,N-Diisopropylchlorophosphoramindite" and insert -- 2-Cyanoethyl N,N-Diisopropylchlorophosphoramidite --.

Column 35, Line 23 (approx.), delete "[M–H]$^{31}$" and insert -- [M–H]$^-$ --.

Column 36, Line 4, delete "[M–H]$^+$" and insert -- [M+H]$^+$ --.

Column 36, Line 64, delete "stifling." and insert -- stirring --.

Signed and Sealed this
Twenty-fifth Day of March, 2025

Coke Morgan Stewart
*Acting Director of the United States Patent and Trademark Office*

Column 39, Lines 2-5, delete " 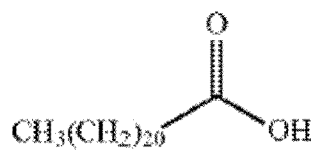 Behenic acid " and insert -- CH₃(CH₂)₁₂COOH --.

Column 41, Line 8, delete "stifling." and insert -- stirring. --.

Column 41, Line 14, delete "[M+AcOH–H]³¹" and insert -- [M+AcOH–H]⁻ --.

Column 47-48, Lines 45-50 (approx.), delete

" 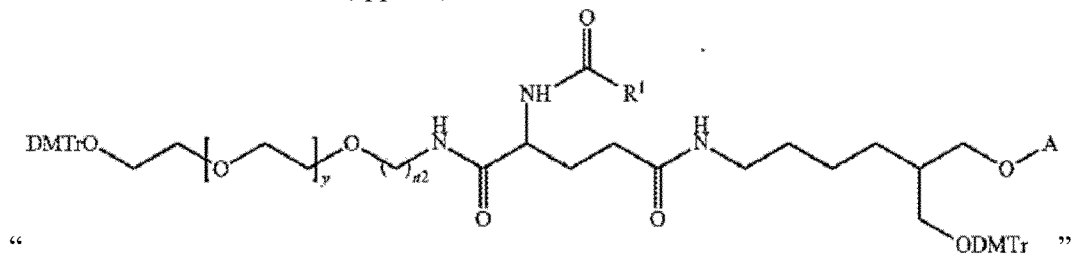 "

and insert -- 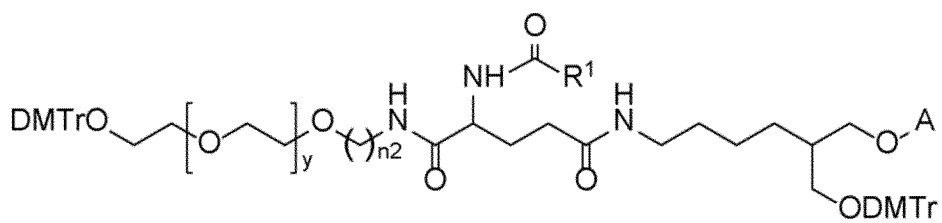 (Ic), where A is succinated CGP or phosphoramidite --.

Column 57, Line 5, delete "0.2 1.µmol." and insert -- 0.2 µmol. --.

Column 58, Line 19 (approx.), delete "0.5-2 1.µmol." and insert -- 0.5-2 µmol. --.

In the Claims

Column 62, Claim 15, Lines 40-45 (approx.), delete " 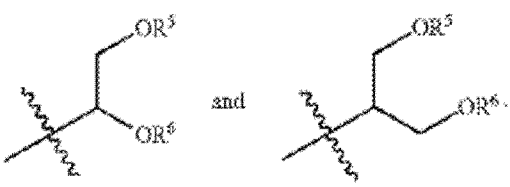 " and insert -- 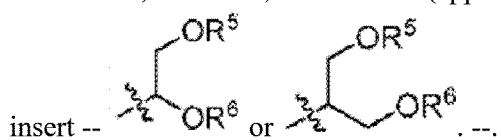 . --.

CERTIFICATE OF CORRECTION (continued)
U.S. Pat. No. 12,098,371 B2

Column 66, Claim 22, Lines 6-13 (approx.), delete " 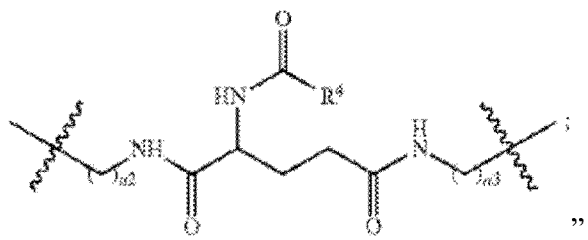 "
and insert -- 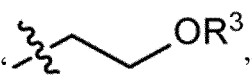 --.

Column 66, Claim 22, Lines 18-20 (approx.), delete " 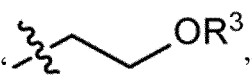 " and insert
-- 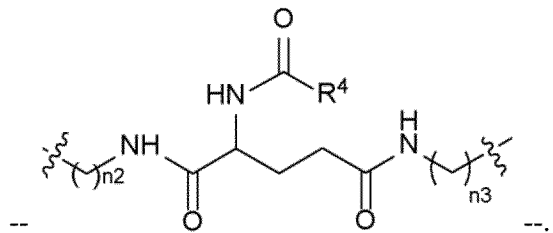 --.

Column 66, Claim 22, Line 24 (approx.), delete "a moiety of $R^6$;" and insert -- a moiety of $R^6$: --.